US012788464B2

(12) United States Patent
Marass et al.

(10) Patent No.: US 12,788,464 B2
(45) Date of Patent: Nov. 10, 2026

(54) SYSTEMS AND METHODS FOR ISOLATING WIRES IN ELECTROPORATION DEVICES

(71) Applicant: St. Jude Medical, Cardiology Division, Inc., St. Paul, MN (US)

(72) Inventors: Timothy S. Marass, Minneapolis, MN (US); Varun Bansal, Maple Grove, MN (US); Jodee M. Maes, Minneapolis, MN (US); Zachary Helgeson, Richfield, MN (US); Isaac Remer, Richfield, MN (US); Dominic J. Leyden, St. Paul, MN (US); Bruce W. Ebner, Shorewood, MN (US); Xuan Khieu, Maple Grove, MN (US); Neil Hawkinson, Ramsey, MN (US); Andrew Oliverius, Zimmerman, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 227 days.

(21) Appl. No.: 18/569,772

(22) PCT Filed: Jun. 14, 2022

(86) PCT No.: PCT/US2022/033352
§ 371 (c)(1),
(2) Date: Dec. 13, 2023

(87) PCT Pub. No.: WO2022/266043
PCT Pub. Date: Dec. 22, 2022

(65) Prior Publication Data

US 2024/0277392 A1 Aug. 22, 2024

Related U.S. Application Data

(60) Provisional application No. 63/210,098, filed on Jun. 14, 2021.

(51) Int. Cl.
*A61B 18/12* (2006.01)
*A61B 18/00* (2006.01)
*A61B 34/20* (2016.01)

(52) U.S. Cl.
CPC .............. *A61B 18/00* (2013.01); *A61B 34/20* (2016.02); *A61B 2018/00083* (2013.01);
(Continued)

(58) Field of Classification Search
CPC ................ A61B 18/00; A61B 18/1492; A61B 2018/00351; A61B 2018/00613;
(Continued)

(56) References Cited

U.S. PATENT DOCUMENTS 5,324,284 A * 6/1994 Imran ................ A61B 18/1492 600/374
5,800,482 A * 9/1998 Pomeranz .............. A61N 1/056 606/41
(Continued)

FOREIGN PATENT DOCUMENTS

EP 0787019 A1 8/1997
JP 2002537059 A 11/2002
(Continued)

OTHER PUBLICATIONS

PCT International Search Report and Written Opinion, Application No. PCT/US2022/033352, dated Oct. 20, 2022, 12 pages.

*Primary Examiner* — Daniel W Fowler
(74) *Attorney, Agent, or Firm* — DENTONS Durham Jones Pinegar

(57) ABSTRACT

Systems and methods for electroporation catheters are provided herein. An electroporation catheter includes a shaft, and a variable diameter loop coupled to a distal end of the shaft, the variable diameter loop including a plurality of electrodes. The catheter further includes a plurality of elec-
(Continued)

trical wires connected to the plurality of electrodes and extending through the variable diameter loop and the shaft, the plurality of electrical wires configured to energize the plurality of electrodes, and a multi-lumen arrangement extending through at least a portion of at least one of the shaft and the variable diameter loop. The multi-lumen arrangement includes a first lumen housing a first subset of the plurality of electrical wires, and a second lumen housing a second subset of the plurality of electrical wires.

27 Claims, 14 Drawing Sheets

(52) U.S. Cl.
CPC ............... *A61B 2018/00166* (2013.01); *A61B 2018/00178* (2013.01); *A61B 2018/00351* (2013.01); *A61B 2018/00577* (2013.01); *A61B 2018/00613* (2013.01); *A61B 2018/00702* (2013.01); *A61B 2018/00761* (2013.01); *A61B 2018/00839* (2013.01); *A61B 2018/00946* (2013.01); *A61B 2018/00952* (2013.01); *A61B 2034/2051* (2016.02)

(58) Field of Classification Search
CPC ........... A61B 2018/00702; A61B 2018/00761; A61B 2018/00946; A61B 2018/126; A61B 2018/1407
See application file for complete search history.

(56) References Cited

U.S. PATENT DOCUMENTS

| | | | | |
|---|---|---|---|---|
| 6,183,463 | B1 * | 2/2001 | Webster, Jr. | A61B 18/1492 604/95.01 |
| 6,283,959 | B1 * | 9/2001 | Lalonde | A61B 18/02 606/23 |
| 6,595,989 | B1 * | 7/2003 | Schaer | A61B 17/22004 606/41 |
| 7,263,397 | B2 | 8/2007 | Hauck et al. | |
| 7,536,218 | B2 | 5/2009 | Govari et al. | |
| 2004/0231683 | A1 * | 11/2004 | Eng | A61B 34/73 606/41 |
| 2006/0184106 | A1 * | 8/2006 | McDaniel | A61B 18/1492 604/95.04 |
| 2006/0264925 | A1 * | 11/2006 | Sharareh | A61B 18/1492 606/41 |
| 2007/0129719 | A1 * | 6/2007 | Kendale | A61B 1/00096 606/41 |
| 2009/0248012 | A1 * | 10/2009 | Maor | A61B 18/14 606/41 |
| 2011/0218528 | A1 * | 9/2011 | Ogata | A61B 18/1492 606/159 |
| 2012/0065633 | A1 * | 3/2012 | Yagi | A61B 18/04 606/28 |
| 2012/0143182 | A1 * | 6/2012 | Ullrich | A61B 18/1445 606/49 |
| 2012/0197246 | A1 * | 8/2012 | Mauch | A61B 18/1492 606/41 |
| 2013/0338467 | A1 | 12/2013 | Grasse et al. | |
| 2014/0261985 | A1 * | 9/2014 | Selkee | A61B 5/6852 156/187 |
| 2017/0035498 | A1 * | 2/2017 | Boden | A61B 18/1492 |
| 2017/0065343 | A1 * | 3/2017 | Mickelsen | A61B 18/1492 |
| 2018/0078738 | A1 * | 3/2018 | Yazdanpanah | A61M 25/0009 |
| 2019/0076179 | A1 | 3/2019 | Babkin et al. | |
| 2019/0117113 | A1 | 4/2019 | Curran | |
| 2019/0160256 | A1 * | 5/2019 | Tegg | A61B 18/14 |
| 2019/0183378 | A1 | 6/2019 | Mosesov et al. | |
| 2019/0239812 | A1 * | 8/2019 | Botzer | A61M 25/005 |
| 2019/0307500 | A1 * | 10/2019 | Byrd | A61B 18/1233 |
| 2019/0357790 | A1 * | 11/2019 | Masuda | A61B 5/6852 |
| 2020/0269038 | A1 | 8/2020 | Paul et al. | |

FOREIGN PATENT DOCUMENTS

| | | | |
|---|---|---|---|
| JP | 2014502195 | A | 1/2014 |
| JP | 2016097307 | A | 5/2016 |
| JP | 2016525416 | A | 8/2016 |
| JP | 2017159056 | A | 9/2017 |
| JP | 2020532408 | A | 11/2020 |
| WO | 2014025394 | A1 | 2/2014 |
| WO | 2015103530 | A1 | 7/2015 |
| WO | 2018102376 | A1 | 6/2018 |
| WO | 2018201037 | A1 | 11/2018 |

* cited by examiner

SYSTEMS AND METHODS FOR ISOLATING WIRES IN ELECTROPORATION DEVICES

This application claims priority to international application No. PCT/US2022/033352, filed Jun. 14, 2022, which claims priority to U.S. Provisional Application No. 63/210,098, filed on Jun. 14, 2021, the entire contents of which are hereby incorporated herein by reference.

FIELD OF THE DISCLOSURE

The present disclosure relates generally to tissue ablation systems. In particular, the present disclosure relates to isolating wires from one another in an electroporation catheter.

BACKGROUND

It is generally known that ablation therapy may be used to treat various conditions afflicting the human anatomy. For example, ablation therapy may be used in the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue apoptosis in cardiac tissue to correct conditions such as atrial arrhythmia (including, but not limited to, ectopic atrial tachycardia, atrial fibrillation, and atrial flutter).

Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Electroporation is a non-thermal ablation technique that involves applying strong electric-fields that induce pore formation in the cellular membrane. The electric field may be induced by applying a relatively short duration pulse which may last, for instance, from a nanosecond to several milliseconds. Such a pulse may be repeated to form a pulse train. When such an electric field is applied to tissue in an in vivo setting, the cells in the tissue are subjected to transmembrane potential, which opens the pores on the cell wall. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation.

For catheters used to deliver bipolar energy using irreversible electroporation (IRE) or pulsed field ablation (PFA) it is important to provide sufficient electrical isolation and dielectric strength resistance between different electrical wires routed through such catheters. For example, a catheter may include a plurality of electrodes, and a pair of those electrodes may function as an electrical bipole pair. In such circumstances, it is important to electrically isolate the electrical wire connected to a first electrode of the pair from the electrical wire connected to the second electrode of the pair.

BRIEF SUMMARY OF THE DISCLOSURE

In one aspect, an electroporation catheter is provided. The catheter includes a shaft, and a variable diameter loop coupled to a distal end of the shaft, the variable diameter loop including a plurality of electrodes. The catheter further includes a plurality of electrical wires connected to the plurality of electrodes and extending through the variable diameter loop and the shaft, the plurality of electrical wires configured to energize the plurality of electrodes, and a multi-lumen arrangement extending through at least a portion of at least one of the shaft and the variable diameter loop. The multi-lumen arrangement includes a first lumen housing a first subset of the plurality of electrical wires, and a second lumen housing a second subset of the plurality of electrical wires.

In another aspect, an electroporation catheter is provided. The catheter includes a variable diameter loop coupled to a distal end of the shaft, the variable diameter loop including a plurality of electrodes, and a plurality of electrical wires connected to the plurality of electrodes and extending through the variable diameter loop and the shaft, the plurality of electrical wires configured to energize the plurality of electrode. The catheter further includes a tubing arrangement extending through at least a portion of at least one of the shaft and the variable diameter loop, the tubing arrangement including a first tube housing a first subset of the plurality of electrical wires, wherein a second subset of the plurality of electrical wires are outside of the first tube and physically isolated from the first subset of the plurality of electrical wires.

In yet another aspect, a method of assembling an electroporation catheter is provided. The method includes coupling a shaft to a variable diameter loop, the variable diameter loop including a plurality of electrodes, connecting a plurality of electrical wires to the plurality of electrodes, the plurality of electrical wires extending through the variable diameter loop and the shaft, the plurality of electrical wires configured to energize the plurality of electrodes, and implementing at least one of a multi-lumen arrangement and a tubing arrangement to physically isolate a first subset of the plurality of electrical wires from a second subset of the plurality of electrical wires.

The foregoing and other aspects, features, details, utilities and advantages of the present disclosure will be apparent from reading the following description and claims, and from reviewing the accompanying drawings.

DETAILED DESCRIPTION OF THE DISCLOSURE

Systems and methods for electroporation catheters are provided herein. An electroporation catheter includes a shaft, and a variable diameter loop coupled to a distal end of the shaft, the variable diameter loop including a plurality of electrodes. The catheter further includes a plurality of electrical wires connected to the plurality of electrodes and extending through the variable diameter loop and the shaft, the plurality of electrical wires configured to energize the plurality of electrodes, and a multi-lumen arrangement extending through at least a portion of at least one of the shaft and the variable diameter loop. The multi-lumen arrangement includes a first lumen housing a first subset of the plurality of electrical wires, and a second lumen housing a second subset of the plurality of electrical wires.

Although an exemplary embodiment of the present disclosure is described with respect to pulmonary vein isolation (PVI), it is contemplated that the described features and methods of the present disclosure as described herein may be incorporated into any number of systems and any number of applications as would be appreciated by one of ordinary skill in the art based on the disclosure herein.

Figure 1A:
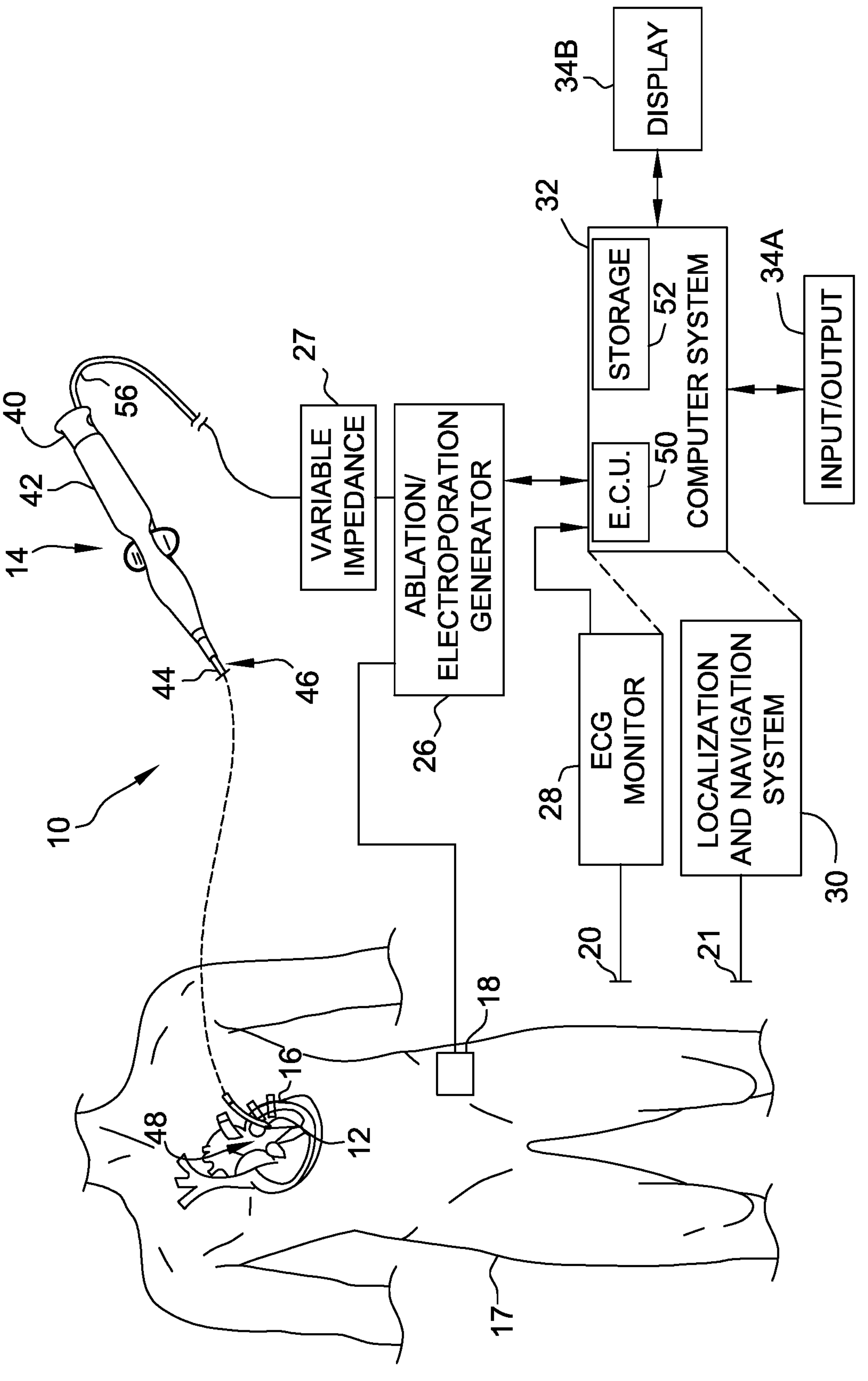
FIG. 1A is a schematic and block diagram view of a system for electroporation therapy.

FIG. 1A is a block diagram view of a system 10 for electroporation therapy. In general, system 10 includes a catheter electrode assembly 12 disposed at a distal end 48 of a catheter 14. As used herein, "proximal" refers to a direction toward the end of the catheter near the clinician and "distal" refers to a direction away from the clinician and (generally) inside the body of a patient. The electrode assembly includes one or more individual, electrically-isolated electrode elements. Each electrode element, also referred to herein as a catheter electrode, is individually wired such that it can be selectively paired or combined with any other electrode element to act as a bipolar or a multi-polar electrode.

System 10 may be used for irreversible electroporation (IRE) to destroy tissue. In particular, system 10 may be used for electroporation-induced primary apoptosis therapy, which refers to the effects of delivering electrical current in such a manner as to directly cause an irreversible loss of plasma membrane (cell wall) integrity leading to its breakdown and cell apoptosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration pulses (e.g., having a 0.1 to 20 millisecond (ms) duration) between closely spaced electrodes capable of delivering an electric field strength of about 0.1 to 1.0 kilovolts/centimeter (kV/cm). System 10 may be used, for example, with a high output loop catheter (See FIGS. 1B and 1C) for high output (e.g., high voltage and/or high current) electroporation procedures. In some particular embodiments, system 10 is configured to deliver an electroporation pulse signal having a relatively high voltage and low pulse duration.

In one embodiment, all electrodes of the loop catheter deliver an electric current simultaneously. Alternatively, in other embodiments, stimulation is delivered between pairs of electrodes on the loop catheter. Delivering electric current simultaneously using a plurality of electrodes arranged in a circular fashion facilitates creating a sufficiently deep lesion for electroporation. To facilitate activating electrodes simultaneously, the electrodes may be switchable between being connected to a 3D mapping system and being connected to EP amplifiers. For a loop catheter, when the loop diameter is minimized, multiple electrodes may overlap with one another.

Irreversible electroporation through a multi-electrode loop catheter may enable pulmonary vein isolation in as few as one shock per vein, which may produce much shorter procedure times compared to sequentially positioning a radiofrequency (RF) ablation tip around a vein.

It should be understood that while the energization strategies are described as involving DC pulses, embodiments may use variations and remain within the spirit and scope of the disclosure. For example, exponentially-decaying pulses, exponentially-increasing pulses, and combinations may be used. Further, in some embodiments, AC pulses may be used.

Further, it should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics.

With this background, and now referring again to FIG. 1A, system 10 includes a catheter electrode assembly 12 including at least one catheter electrode. Electrode assembly 12 is incorporated as part of a medical device such as a catheter 14 for electroporation therapy of tissue 16 in a body 17 of a patient. In the illustrative embodiment, tissue 16 includes heart or cardiac tissue. It should be understood, however, that embodiments may be used to conduct electroporation therapy with respect to a variety of other body tissues.

FIG. 1A further shows a plurality of return electrodes designated 18, 20, and 21, which are diagrammatic of the body connections that may be used by the various subsystems included in overall system 10, such as an electroporation generator 26, an electrophysiology (EP) monitor such as an ECG monitor 28, and a localization and navigation system 30 for visualization, mapping, and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode, and may include split patch electrodes (as described herein). In other embodiments, return electrodes 18, 20, and 21 may be any other type of electrode suitable for use as a return electrode including, for example, one or more catheter electrodes. Return electrodes that are catheter electrodes may be part of electrode assembly 12 or part of a separate catheter or device (not shown). System 10 may further include a main computer system 32 (including an electronic control unit 50 and data storage-memory 52), which may be integrated with localization and navigation system 30 in certain embodiments. System 32 may further include conventional interface components, such as various user input/output mechanisms 34A and a display 34B, among other components.

Electroporation generator 26 is configured to energize the electrode element(s) in accordance with an electroporation energization strategy, which may be predetermined or may be user-selectable. For electroporation-induced primary apoptosis therapy, generator 26 may be configured to produce an electric current that is delivered via electrode assembly 12 as a pulsed electric field in the form of short-duration DC pulses (e.g., a nanosecond to several milliseconds duration, a 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

Electroporation generator 26, sometimes also referred to herein as a DC energy source, is a monophasic electroporation generator 26 configured to generate a series of DC energy pulses that all produce current in the same direction. In other embodiments, electroporation generator is biphasic or polyphasic electroporation generator configured to produce DC energy pulses that do not all produce current in the same direction. In some embodiments, for example, the electroporation generator 26 is configured to deliver a biphasic, symmetric pulse signal in which a first (e.g., positive) phase of the signal has the same or similar voltage amplitude and pulse duration as the second (i.e., negative) phase of the signal. In other embodiments, the electroporation generator 26 is configured to deliver a biphasic, asymmetric pulse signal in which a first (e.g., positive) phase of the signal has a different voltage amplitude and/or duration as the second (i.e., negative) phase of the signal. Several exemplary electroporation energization schemes are described in U.S. application Ser. No. 17/247,198, filed on Dec. 3, 2020, the contents of which are incorporated herein by reference in its entirety.

In some embodiments, electroporation generator 26 is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. For example, electroporation generator 26 may output a DC pulse having a peak magnitude from about 300 Volts (V) to about 3,200 V at the two hundred joule output level. In some embodiments, the peak magnitude may be even larger (e.g., on the order of 10,000 V). Other embodiments may output any other suitable positive or negative voltage. For example, in some embodiments, the systems and methods described herein may include pulses with amplitudes from about 500 V to about 4,000 V, with pulse widths from about 200 nanoseconds to about 20 microseconds.

In some embodiments, a variable impedance 27 allows the impedance of system 10 to be varied to limit arcing. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26.

With continued reference to FIG. 1A, as noted above, catheter 14 may include functionality for electroporation and in certain embodiments also other types of ablation (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal 48 end. Catheter 14 may also include other conventional components not illustrated herein such as a temperature sensor, additional electrodes, and corresponding conductors or leads. Connector 40 provides mechanical and electrical connection(s) for cable 56 extending from generator 26. Connector 40 may include conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, and/or orientation of a portion of the catheter, and it will be understood that the construction of handle 42 may vary. In an alternate embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments.

Shaft 44 may be made from conventional materials such as polyurethane and defines one or more lumens configured to house and/or transport electrical conductors, fluids or surgical tools, as described herein. Shaft 44 may be introduced into a blood vessel or other structure within body 17 through a conventional introducer. Shaft 44 may then be advanced/retracted and/or steered or guided through body 17 to a desired location such as the site of tissue 16, including through the use of guidewires or other means known in the art.

In some embodiments, catheter 14 is a loop catheter having catheter electrodes (not shown in FIG. 1A) distributed at the distal end of shaft 44. The diameter of the loop may be variable. In some embodiments, the loop catheter has a maximum diameter of about twenty-seven millimeters (mm). In some embodiments, the loop diameter is variable between about fifteen mm and about twenty eight mm. Alternatively, the catheter may be a fixed diameter loop catheter or may be variable between different diameters. In some embodiments, catheter 14 has fourteen catheter electrodes. In other embodiments, catheter 14 includes ten catheter electrodes, twenty catheter electrodes, or any other suitable number of electrodes for performing electroporation. In some embodiments, the catheter electrodes are ring electrodes, such as platinum ring electrodes. Alternatively, the catheter electrodes may be any other suitable type of electrodes, such as partial ring electrodes or electrodes printed on a flex material. In various embodiments, the catheter electrodes have lengths of 1.0 mm, 2.0 mm, 2.5 mm, and/or any other suitable length for electroporation.

Localization and navigation system 30 may be provided for visualization, mapping and navigation of internal body structures. Localization and navigation system 30 may include conventional apparatus known generally in the art (e.g., an EnSite Precision™ System, commercially available from Abbott Laboratories. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is an example only, and is not limiting in nature. Other technologies for locating/navigating a catheter in space (and for visualization) are known, including for example, the CARTO navigation and location system of Biosense Webster, Inc., the Rhythmia® system of Boston Scientific Schimed, Inc., the KODEX® system of Koninklijke Philips N.V., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system. As yet another example, system 10 may utilize a combination electric field-based and magnetic field-based system as generally shown with reference to U.S. Pat. No. 7,536,218 entitled "Hybrid Magnetic-Based and Impedance Based Position Sensing," the disclosure of which is incorporated herein by reference in its entirety.

Figure 1B:
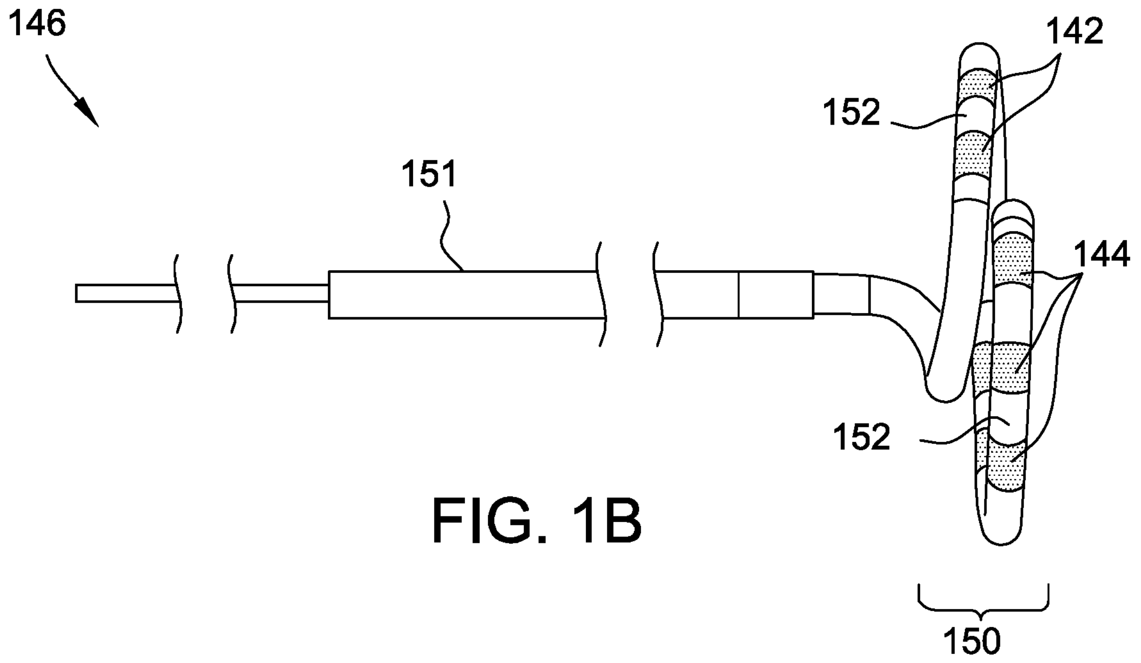
FIGS. 1B and 1C are views of one embodiment of a distal loop subassembly that may be used with the catheter shown in FIG. 1A.
Figure 1C:
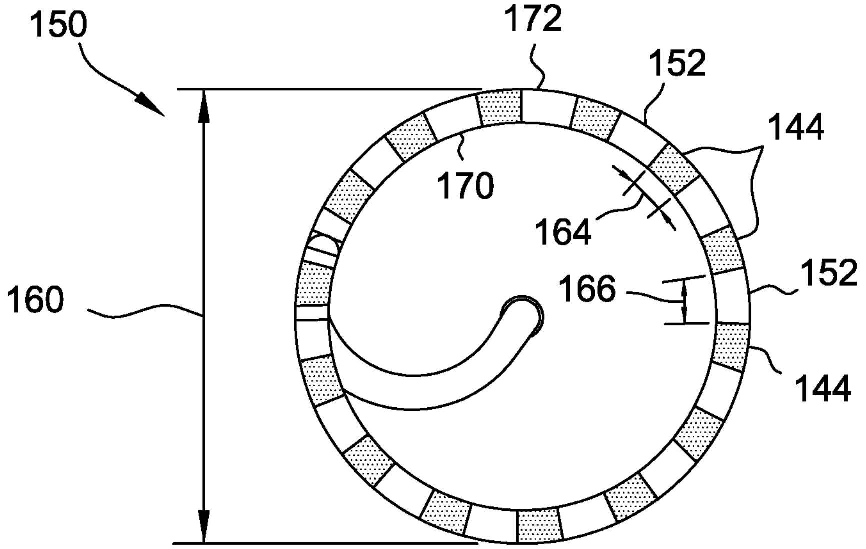

FIGS. 1B and 1C are views of one embodiment of a distal loop subassembly 146 that may be used with catheter 14 in system 10. Those of skill in the art will appreciate that, in other embodiments, any suitable catheter may be used. Specifically, FIG. 1B is a side view of distal loop subassembly 146 with a variable diameter loop 150 at a distal end 142. FIG. 1C is an end view of variable diameter loop 150 of distal loop subassembly 146. Those of skill in the art will appreciate that, although the embodiments disclosed herein are discussed in the context of a variable diameter loop, the methods and systems described herein may be implemented using any suitable catheter (e.g., fixed loop catheters, linear catheters, etc.). As shown in FIGS. 1B and 1C, variable diameter loop 150 is coupled to a distal section 151 of shaft 44.

Variable diameter loop 150 is selectively transitionable between an expanded (also referred to as "open") diameter 160 (shown in FIG. 1C) and a retracted (also referred to as "closed") diameter 160 (not shown). In the example embodiment, an expanded diameter 160 is twenty eight mm and a retracted diameter 160 is fifteen mm. In other embodiments, diameter 160 may be variable between any suitable open and closed diameters 160.

In the embodiment shown, variable diameter loop 150 includes fourteen catheter electrodes 144 substantially evenly spaced around the circumference of variable diameter loop 150 in the expanded configuration. In the retracted configuration, one or more of electrodes 144 may overlap.

Catheter electrodes 144 are platinum ring electrodes configured to conduct and/or discharge electrical current in the range of one thousand volts and/or ten amperes. In other embodiments, variable diameter loop 150 may include any suitable number of catheter electrodes 144 made of any suitable material. Catheter electrodes 144 may include any catheter electrode suitable to conduct high voltage and/or high current (e.g., in the range of one thousand volts and/or ten amperes). Each catheter electrode 144 is separated from each other catheter electrode by an insulated gap 152. In the example embodiment, each catheter electrode 144 has a same length 164 (shown in FIG. 1C) and each insulated gap 152 has a same length 166 as each other gap 152. Length 164 and length 166 are both about 2.5 mm in the example embodiment. In other embodiments, length 164 and length 166 may be different from each other. Moreover, in some embodiments, catheter electrodes 144 may not all have the same length 164 and/or insulated gaps 152 may not all have the same length 166. In some embodiments, catheter electrodes 144 are not spaced evenly around the circumference of variable diameter loop 150.

Diameter 160 and catheter electrode 144 spacing may be developed to provide a targeted range of energy density to tissue, as well as to provide sufficient electroporation coverage for different human anatomic geometries. In general, a sufficient number of electrodes 144 with appropriate lengths 164 are desired to provide substantially even and continuous coverage around the circumference of variable diameter loop 150, while still allowing enough flexibility to allow variable diameter loop 150 to expand and contract to vary diameter 160 to the desired extremes.

As mentioned above, length 164 of catheter electrodes 144 may be varied. Increasing length 164 of catheter electrodes 144 may increase coverage of electrodes 144 around the circumference of variable diameter loop 150 while also decreasing current density (by increasing the surface area) on electrodes 144, which may help prevent arcing during electroporation operations. Increasing length 164 too much, however, may prevent variable diameter loop 150 from forming a smooth circular shape and may limit the closed diameter 160 of variable diameter loop 150. Additionally, too great a length 164 may increase the surface area of catheter electrodes 144 to a point that the current density applied to catheter electrodes 144 by a power source is below the minimum current density needed for successful therapy. Conversely, decreasing length 164 decreases the surface area, thereby increasing the current density (assuming no other system changes) on catheter electrodes 144. As discussed above, greater current densities may lead to increased risk of arcing during electroporation, and may result in larger additional system resistances needing to be added to prevent arcing. Moreover, in order to get a desired, even coverage about the circumference of variable diameter loop 150, more catheter electrodes 144 may be needed if length 164 is decreased. Increasing the number of catheter electrodes 144 on variable diameter loop 150 may prevent variable diameter loop 150 from being able to be contracted to a desired minimum diameter 160.

Pulsed field ablation (PFA) has been shown to be an effective form of ablation for treatment of cardiac arrhythmias, particularly for instantaneous pulmonary vein isolation (PVI). PFA includes delivering high voltage pulses from electrodes disposed on a catheter (e.g., including variable diameter loop 150). In PFA, for example, voltage amplitudes may range from about 300 V to at least 3,200 V (or even as large as on the order as 10,000 V), and pulse widths may from hundreds of nanoseconds to tens of milliseconds.

These electric fields may be applied between adjacent electrodes (in a bipolar approach) or between a one or more electrodes and a return patch (in a monopolar approach). There are advantages and disadvantages to each of these approaches (e.g., when using variable diameter loop 150).

For lesion size and proximity, the monopolar approach has a wider range of effect, and can potentially create deeper lesions with the same applied voltage. Further, the monopolar approach may be able to create lesions from a distance (e.g., generally proximate, but not necessarily contacting tissue). The bipolar approach may create smaller lesions, requiring closer proximity or contact with tissue to create transmural lesions. However, the monopolar approach may create larger lesions than are necessary, while the lesions generated using the bipolar approach may be more localized.

Due to a wider range of effect, the monopolar approach may cause unwanted skeletal muscle and/or nerve activation. In contrast, the bipolar approach has a constrained range of effect proportional to electrode spacing on the lead, and is less likely to depolarize cardiac myocytes or nerve fibers.

For the monopolar approach, only a single potential is applied in catheter wires and electrodes. Further, because all the electrodes are at the same polarity, the configuration is not susceptible to arcing (e.g., when using variable diameter loop 150). In contrast, for the bipolar approach, the internal architecture of the catheter must be constructed to prevent arcing, as different electrodes are at different potentials. Further, with a catheter having a variable diameter loop at the distal end (e.g., variable diameter loop 150), depending on the size of the loop and the orientation of the catheter, electrodes with opposite polarities may overlap, potentially resulting in arcing or shunted current paths, which is generally undesirable. Further, interleaved electrodes may interfere with signals used for tissue sensing.

To monitor operation of system 10, one or more impedances between catheter electrodes 144 and/or return electrodes 18, 20, and 21 may be measured. For example, for system 10, impedances may be measured as described in U.S. Patent Application Publication No. 2019/0117113, filed on Oct. 23, 2018, U.S. Patent Application Publication No. 2019/0183378, filed on Dec. 19, 2018, and U.S. Patent Application No. 63/027,660, filed on May 20, 2020, all of which are incorporated by reference herein in their entirety.

In the example embodiment, a plurality of wires (not shown in FIGS. 1A-1C) are routed through catheter 14 to enable operation of catheter 14. For example, a shaping wire (to control the shape of variable diameter loop 150), an activation wire (to control the diameter of variable diameter loop 150), and a plurality of electrical wires (to control operation of catheter electrodes 144) may be routed through catheter 14, as described in further detail below.

Figure 2A:
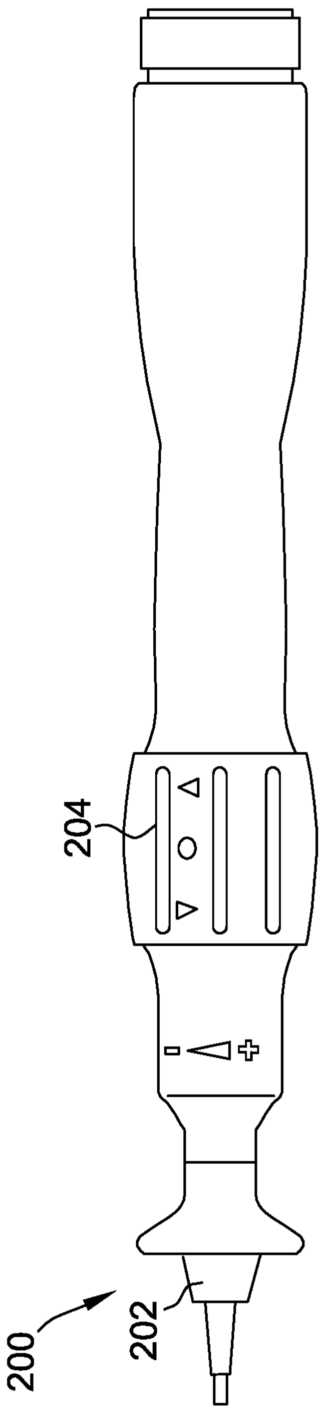
FIG. 2A is a view of one embodiment of a handle that may be used with the system shown in FIG. 1A.

FIG. 2A is a view of one embodiment of a handle 200 that may be used with system 10 and variable diameter loop 150. Handle 200 includes a first actuator 202 and a second actuator 204. First actuator 202 may be, for example, slidable along a longitudinal axis of handle 200 to selectively deflect variable diameter loop 150 relative to shaft 44. Second actuator 204 may be, for example, rotatable about the longitudinal axis of handle 200 to selectively adjust a diameter of variable diameter loop 150. Accordingly, first and second actuators 202 and 204 may be connected to one or more activation wires extending through catheter 14.

Figure 2B:
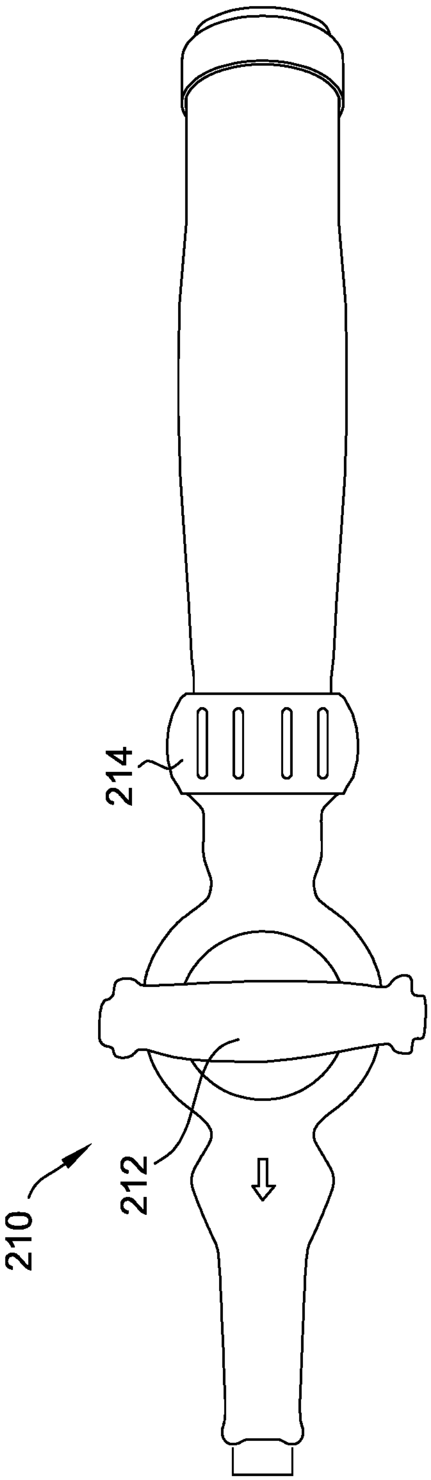
FIG. 2B is a view of another embodiment of a handle that may be used with the system shown in FIG. 1A.

FIG. 2B is a view of another embodiment of a handle 210 that may be used with system 10 and variable diameter loop 150. Handle 210 includes a first actuator 212 and a second actuator 214. First actuator 212 may be, for example, rotatable about a rotational axis that is substantially perpendicular to a longitudinal axis of handle 210 to selectively deflect variable diameter loop 150 relative to shaft 44. Second actuator 214 may be, for example, rotatable about the longitudinal axis of handle 210 to selectively adjust a diameter of variable diameter loop 150. Accordingly, first and second actuators 212 and 214 may be connected to one or more activation wires extending through catheter 14.

Those of skill in the art will appreciate that handles 200 and 210 are merely examples, and that any suitable handles and/or arrangement of actuators may be used to implement the systems and methods described herein.

Figure 3:
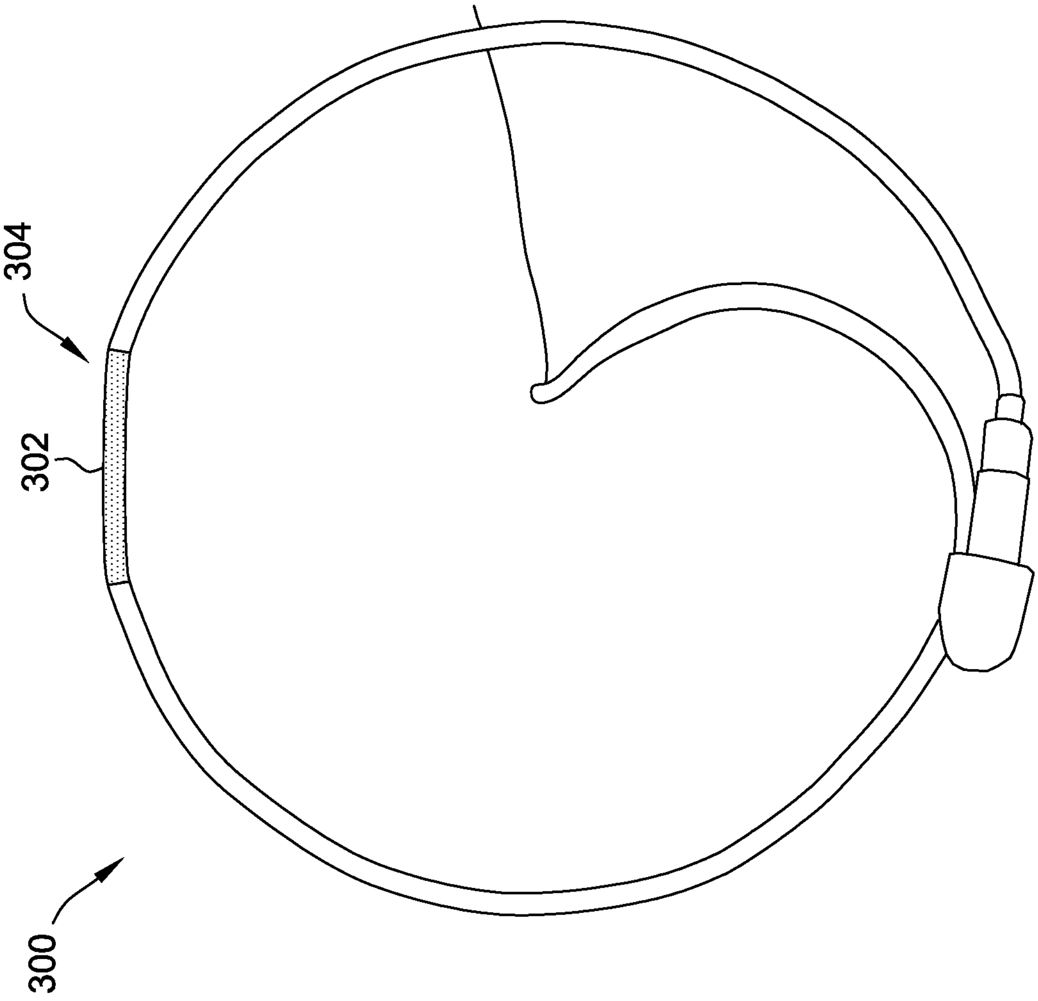
FIG. 3 is a view of one embodiment of a variable diameter loop that may be used with the system shown in FIG. 1A.

FIG. 3 is a view of one embodiment of a variable diameter loop 300 that may be used to implement variable diameter loop 150 (shown in FIGS. 1A and 1B). In this embodiment, variable diameter loop 300 includes a magnetic sensor 302 located at approximately a midpoint 304 of variable diameter loop 300. Alternatively, variable diameter loop 300 may include any suitable number and arrangement of magnetic sensors. In addition to magnetic sensor 302, one or more magnetic sensors (not shown) may also be positioned within shaft 44. Magnetic sensors in variable diameter loop 300 and shaft 44 are facilitate identifying a position and orientation of catheter 14 using localization and navigation system 30 (described above).

Figure 4:
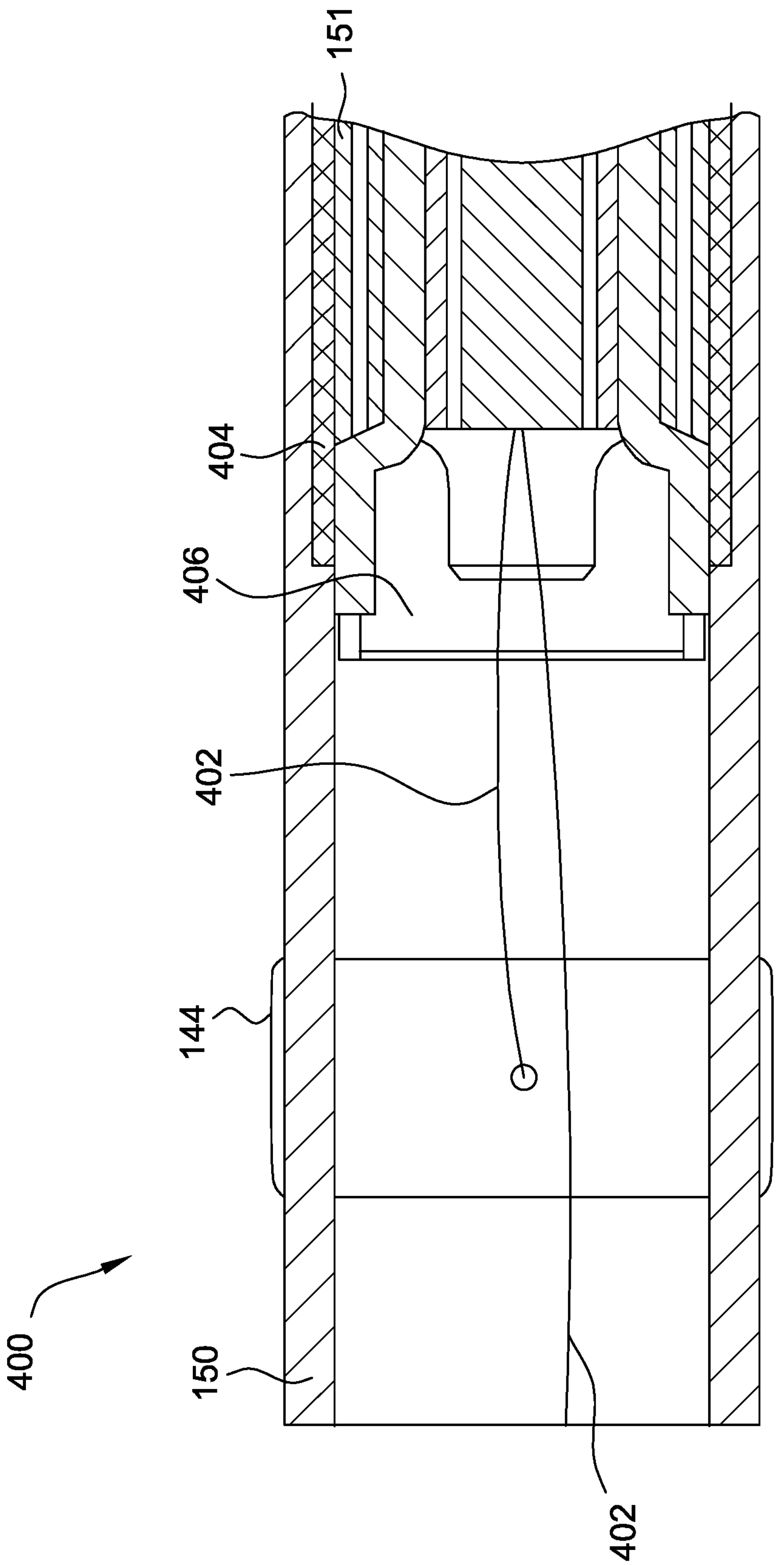
FIG. 4 is a cross-sectional view of one embodiment of a coupling arrangement that may be used with the system shown in FIG. 1A.

FIG. 4 is a cross-sectional view of one embodiment of a coupling arrangement 400 between variable diameter loop 150 and distal section 151 of shaft 44. In FIG. 4, two electrical wires 402 and one catheter electrode 144 are shown, with one of electrical wires 402 coupled to catheter electrode 144. Further, as shown in FIG. 4, a braid 404 (e.g., fabricated from stainless steel) reinforces the coupling arrangement 400. In the embodiment shown, braid 404 extends proximate the middle of a pull ring 406, but does not extend distally to (or beyond) catheter electrode 144. Terminating braid 404 proximal of catheter electrodes 144 prevents braid 440 from potentially interfering with electrical wires 402.

Within catheter 14, it is important to provide sufficient electrical isolation and dielectric strength resistance between positive and negative electrical wires (such as electrical wires 402 (shown in FIG. 4)), in order to avoid electrical breakdown or electrical arcing. In at least some known systems, various wires (e.g., electrical wires, shaping wires, activation wires) are all routed through one lumen (e.g., a lumen formed by the catheter body). However, for irreversible electroporation (IRE)/pulsed field ablation (PFA) catheters, such as catheter 14 (shown in FIG. 1), it may be desirable to improve isolation between the various wires. Accordingly, the systems and methods described herein facilitate isolating various wires from one another in an IRE/PFA catheter. Those of skill in the art will appreciate, however, that the embodiments described herein are not limited to use with IRE/PFA catheters, but may be used with other medical devices as well (e.g., radio-frequency (RF) ablation catheters).

For example, in embodiments where variable diameter loop 150 includes fourteen catheter electrodes 144, a total of fourteen corresponding electrical wires may be routed through variable diameter loop 150. These electrical wires carry relatively high voltage and current when energizing corresponding electrodes. Accordingly, positive and negative wires of the electrical wires should be sufficiently isolated from one another to avoid electrical breakdown or acing. Electrical arcing between two wires may, for example, cause burning or charring of material in catheter 14.

In some embodiments, to isolate various wires from one another, a multi-lumen arrangement is utilized. For example, variable diameter loop 150 is formed from a round tube shaped in a spiral shape. To facilitate operation of variable diameter loop 150, a shaping wire (e.g., a Nitinol wire), and activation wire, and electrical wires are routed thorough the tube. By pulling the activation wire, in some embodiment, variable diameter loop 150 can be straightened out into a linear shape (e.g., to facilitate inserting variable diameter loop 150 though an introducer).

Referring back to FIG. 1C, when variable diameter loop 150 transitions from a spiral shape to a linear shape, wires running along an inner circumference 170 of variable diameter loop 150 are stretched further than wires running along an outer circumference 172 of variable diameter loop. This stretching may cause electrical wires running along inner circumference 170 to break, as the electrical wires are typically bonded in place. The multi-lumen arrangements described herein, in addition to sufficiently isolating the various wires, also prevents stretching and breaking of the electrical wires. Although at least some of the embodiments described herein are described in the context of variable diameter loop 150, those of skill in the art will appreciate that the multi-lumen arrangements described herein may be implemented within variable diameter loop 150 and/or shaft 44. Further, those of skill in the art will appreciate that wire routing configurations described herein are merely examples, and that other wire routing configurations are within the spirit and scope of the disclosure. The multi-lumen arrangements described herein may be fabricated using any suitable technique. For example, in one embodiment, multiple lumens are formed by removing material from a solid cylindrical body. Alternatively, the multi-lumen arrangements described herein may be formed by extruding over thin wall plastic tubes that define the various lumens.

Figure 5A:
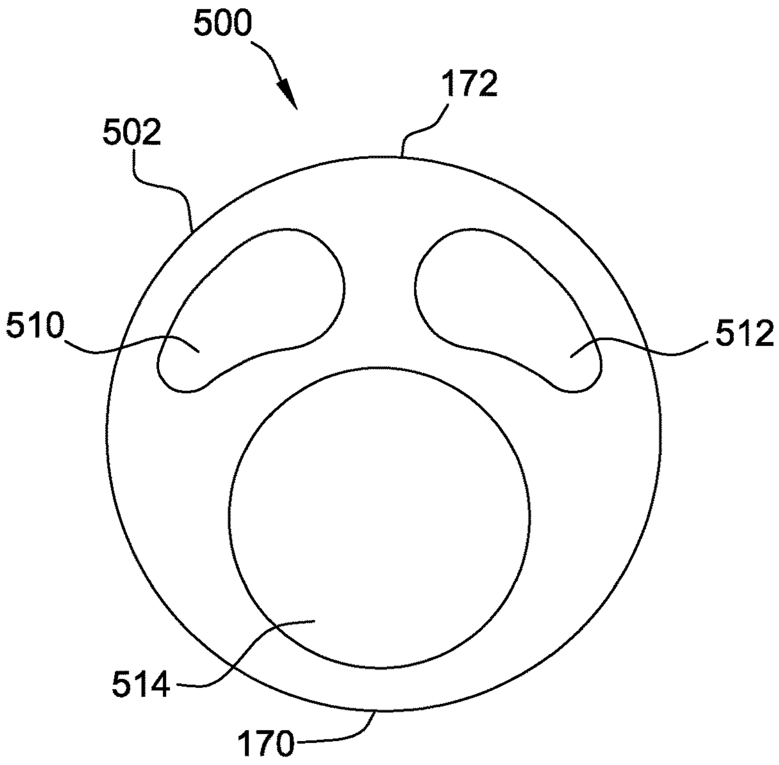
FIG. 5A is an end view of one embodiment of a multi-lumen arrangement.
Figure 5B:
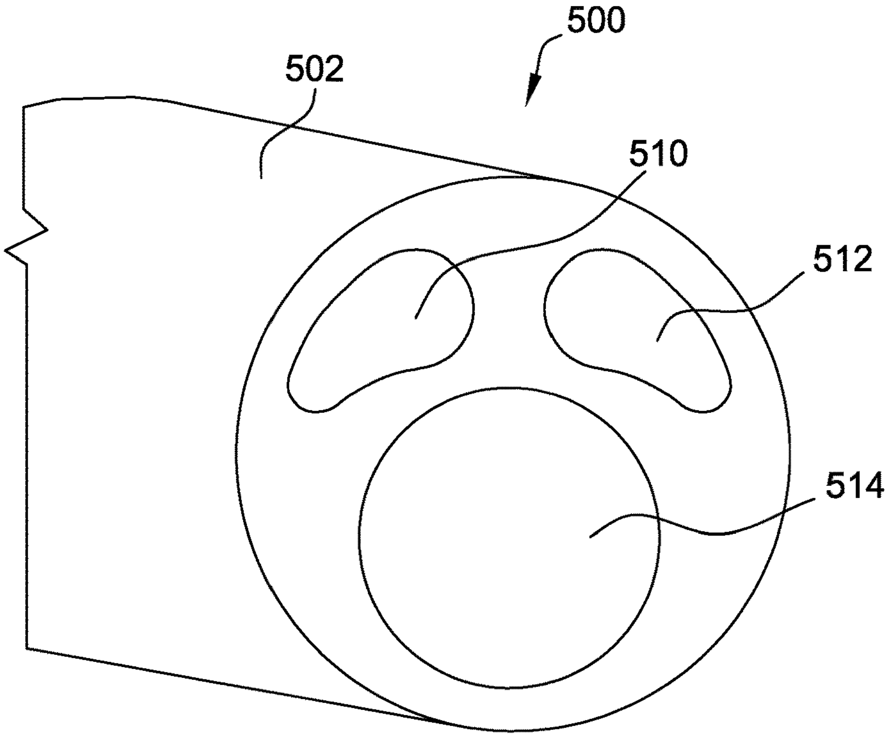
FIG. 5B is perspective view of the multi-lumen arrangement shown in FIG. 5A.

FIG. 5A is an end view of one embodiment of a multi-lumen arrangement 500, and FIG. 5B is a perspective view of multi-lumen arrangement 500. In the embodiment shown in FIGS. 5A and 5B, multi-lumen arrangement 500 includes a tube 502 (e.g., formed by variable diameter loop 150 and/or shaft 44) that defines three lumens: a first lumen 510, a second lumen 512, and a third lumen 514 extending through tube 502. In this embodiment, cross-sections of first and second lumen 510 and 512 are generally teardrop shaped, and the cross-section of third lumen 514 is circular. Alternatively, lumen 510, 512, and 514 may have any suitable shape.

In this embodiment, electrical wires having a first polarity (e.g., positive electrical wires) are routed through first lumen 510, and electrical wires having a second polarity (e.g., negative electrical wires) are routed through second lumen 512. Thus, electrical wires having different polarities are located in different lumens, electrically isolating them from one another. Further, in this embodiment, the shaping wire and activation wire are routed through third lumen 514. Thus, the shaping and activation wires are separated from the electrical wires. Additional wires (e.g., a wire for magnetic sensor 302) may also be routed through third lumen 514.

When located within variable diameter loop 150, first and second lumens 510 and 512 are located opposite inner circumference 170, and proximate outer circumference 172. This configuration prevents electrical wires routed through first and second lumens 510 and 512 from stretching and breaking with variable diameter loop 150 is straightened out.

Figure 6:
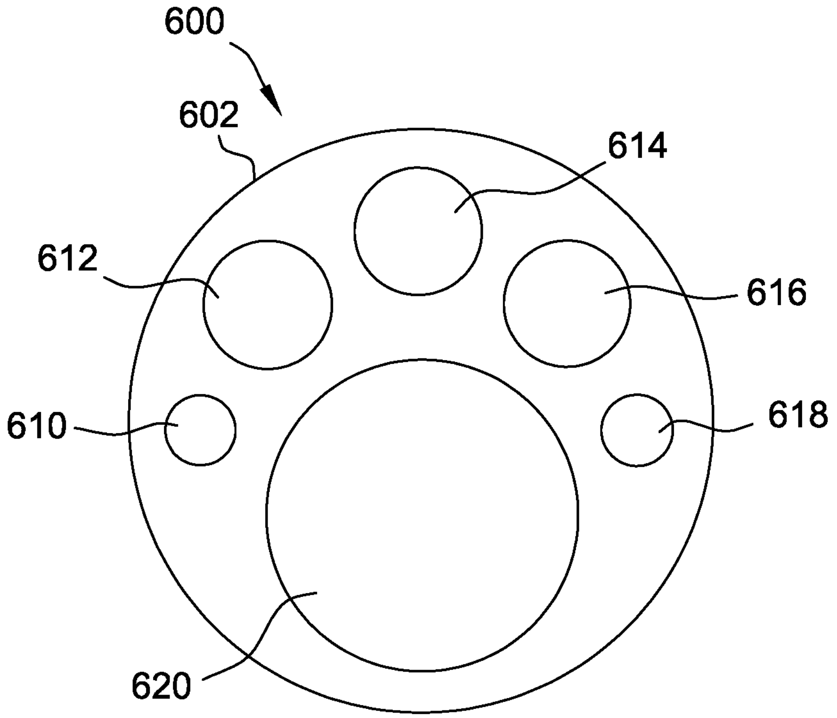
FIG. 6 is an end view of another embodiment of a multi-lumen arrangement.

FIG. 6 is an end view of another embodiment of a multi-lumen arrangement 600. In the embodiment shown in FIG. 6, multi-lumen arrangement 600 includes a tube 602 (e.g., formed by variable diameter loop 150 and/or shaft 44) that defines six lumens: a first lumen 610, a second lumen 612, a third lumen 614, a fourth lumen 616, a fifth lumen 618, and a sixth lumen 620 extending through tube 602. In this embodiment, cross-sections of all lumens 610, 612, 614, 616, 618, and 620 are all circular. Alternatively, lumens 610, 612, 614, 616, 618, and 620 may have any suitable shape.

In this embodiment, electrical wires having a first polarity (e.g., positive electrical wires) are routed through second lumen 612, and electrical wires having a second polarity (e.g., negative electrical wires) are routed through third lumen 614. Thus, electrical wires having different polarities are located in different lumens, electrically isolating them from one another. Further, in this embodiment, the shaping wire and activation wire are routed through sixth lumen 620. Thus, the shaping and activation wires are separated from the electrical wires. Additional wires (e.g., a wire for magnetic sensor 302) may be routed through fourth lumen 616. In this embodiment, first lumen 610 and fifth lumen 618 are dummy lumens that do not carry any wires. First and fifth lumens 610 and 618 do provide a structural benefit, however, as they keep wall thicknesses around second, third, fourth, and sixth lumens 612, 614, 616, and 620 relatively consistent.

Figure 7:
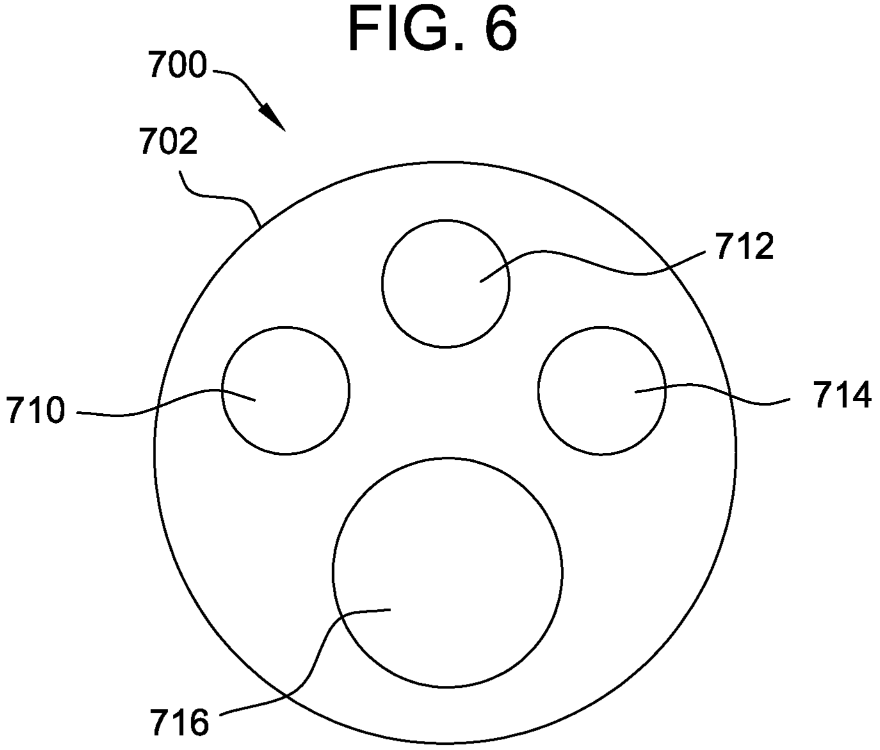
FIG. 7 is an end view of another embodiment of a multi-lumen arrangement.

FIG. 7 is an end view of another embodiment of a multi-lumen arrangement 700. In the embodiment shown in FIG. 7, multi-lumen arrangement 700 includes a tube 702 (e.g., formed by variable diameter loop 150 and/or shaft 44) that defines four lumens: a first lumen 710, a second lumen 712, a third lumen 714, and a fourth lumen 716. In this embodiment, cross-sections of all lumens 710, 712, 714, and 716 are all circular. Alternatively, lumens 710, 712, 714, and 716 may have any suitable shape.

In this embodiment, electrical wires having a first polarity (e.g., positive electrical wires) are routed through first lumen 710, and electrical wires having a second polarity (e.g., negative electrical wires) are routed through second lumen 712. Thus, electrical wires having different polarities are located in different lumens, electrically isolating them from one another. Further, in this embodiment, the shaping wire and activation wire are routed through fourth lumen 716.

Thus, the shaping and activation wires are separated from the electrical wires. Additional wires (e.g., a wire for magnetic sensor 302) may be routed through third lumen 714.

Figure 8:
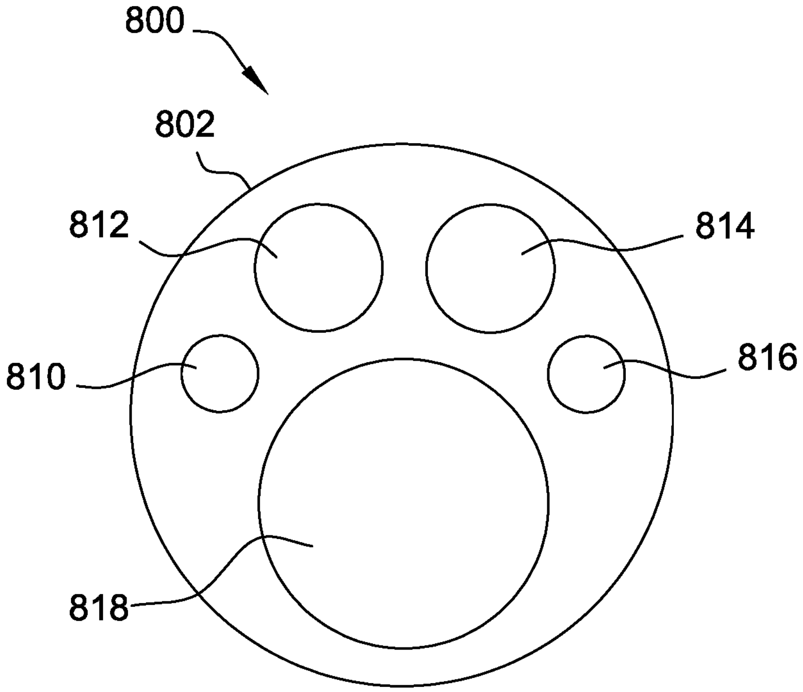
FIG. 8 is an end view of another embodiment of a multi-lumen arrangement.

FIG. 8 is an end view of another embodiment of a multi-lumen arrangement 800. In the embodiment shown in FIG. 8, multi-lumen arrangement 800 includes a tube 802 (e.g., formed by variable diameter loop 150 and/or shaft 44) that defines five lumens: a first lumen 810, a second lumen 812, a third lumen 814, a fourth lumen 816, and a fifth lumen 818. In this embodiment, cross-sections of all lumens 810, 812, 814, 816, and 818 are all circular. Alternatively, lumens 810, 812, 814, 816, and 818 may have any suitable shape.

In this embodiment, electrical wires having a first polarity (e.g., positive electrical wires) are routed through second lumen 812, and electrical wires having a second polarity (e.g., negative electrical wires) are routed through third lumen 814. Thus, electrical wires having different polarities are located in different lumens, electrically isolating them from one another. Further, in this embodiment, the shaping wire and activation wire are routed through fifth lumen 818. Thus, the shaping and activation wires are separated from the electrical wires. Additional wires (e.g., a wire for magnetic sensor 302) may also be routed through fifth lumen 818. In this embodiment, first lumen 810 and fourth lumen 816 are dummy lumens that do not carry any wires. First and fourth lumens 810 and 816 do provide a structural benefit, however, as they keep wall thicknesses around second, third, and fifth lumens 812, 814, and 818 relatively consistent.

Figure 9:
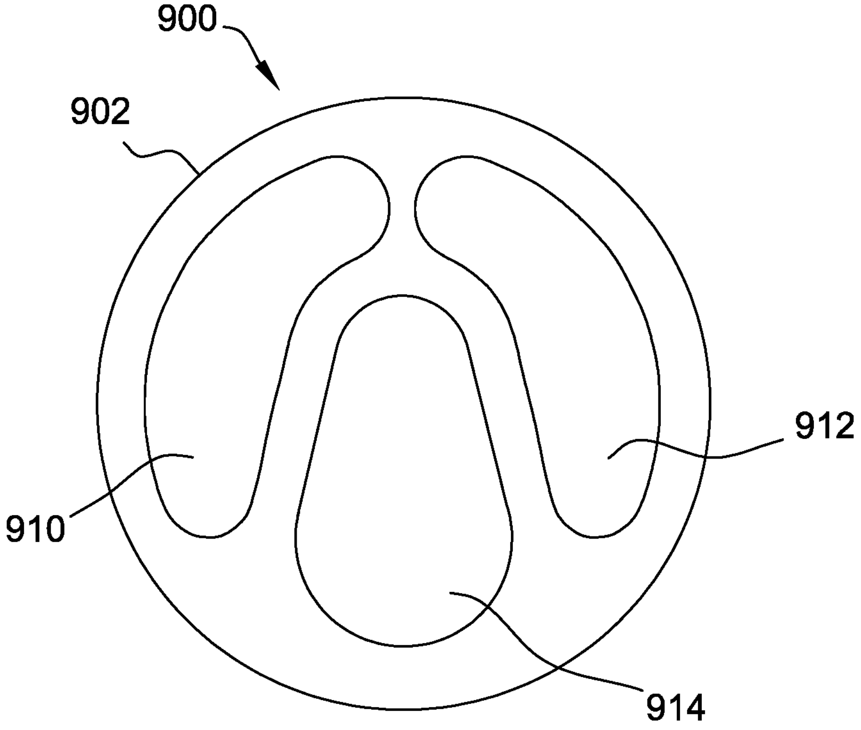
FIG. 9 is an end view of another embodiment of a multi-lumen arrangement.

FIG. 9 is an end view of another embodiment of a multi-lumen arrangement 900. In the embodiment shown in FIG. 9, multi-lumen arrangement 900 includes a tube 902 (e.g., formed by variable diameter loop 150 and/or shaft 44) that defines three lumens: a first lumen 910, a second lumen 912, and a third lumen 914. In this embodiment, cross-sections of first and second lumens 910 and 912 are generally kidney shaped, and the cross-section of third lumen 914 is generally teardrop shaped. The shape of lumens 910, 912, and 914 keep wall thicknesses around lumens 910, 912, and 914 relatively consistent. Alternatively, lumens 910, 912, and 914 may have any suitable shape.

In this embodiment, electrical wires having a first polarity (e.g., positive electrical wires) are routed through first lumen 910, and electrical wires having a second polarity (e.g., negative electrical wires) are routed through second lumen 912. Thus, electrical wires having different polarities are located in different lumens, electrically isolating them from one another. Further, in this embodiment, the shaping wire and activation wire are routed through third lumen 914. Thus, the shaping and activation wires are separated from the electrical wires. Additional wires (e.g., a wire for magnetic sensor 302) may also be routed through third lumen 914.

Figure 10:
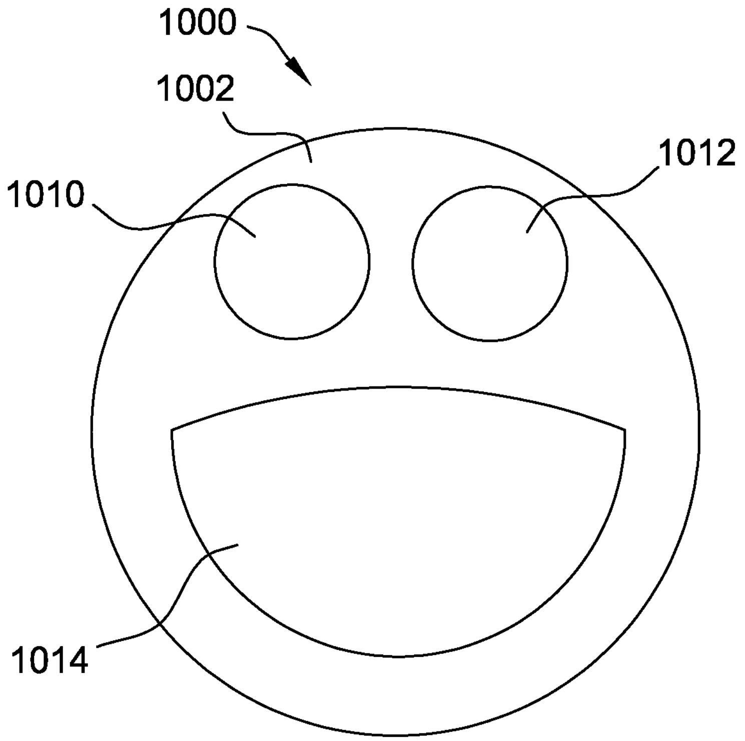
FIG. 10 is an end view of another embodiment of a multi-lumen arrangement.

FIG. 10 is an end view of another embodiment of a multi-lumen arrangement 1000. In the embodiment shown in FIG. 10, multi-lumen arrangement 1000 includes a tube 1002 (e.g., formed by variable diameter loop 150 and/or shaft 44) that defines three lumens: a first lumen 1010, a second lumen 1012, and a third lumen 1014. In this embodiment, cross-sections of first and second lumens 1010 and 1012 are generally circular, and the cross-section of third lumen 1014 has a bulbous shape. Alternatively, lumens 1010, 1012, and 1014 may have any suitable shape.

In this embodiment, electrical wires having a first polarity (e.g., positive electrical wires) are routed through first lumen 1010, and electrical wires having a second polarity (e.g., negative electrical wires) are routed through second lumen 1012. Thus, electrical wires having different polarities are located in different lumens, electrically isolating them from one another. Further, in this embodiment, the shaping wire and activation wire are routed through third lumen 1014. Thus, the shaping and activation wires are separated from the electrical wires. Additional wires (e.g., a wire for magnetic sensor 302) may also be routed through third lumen 1014.

Figure 11:
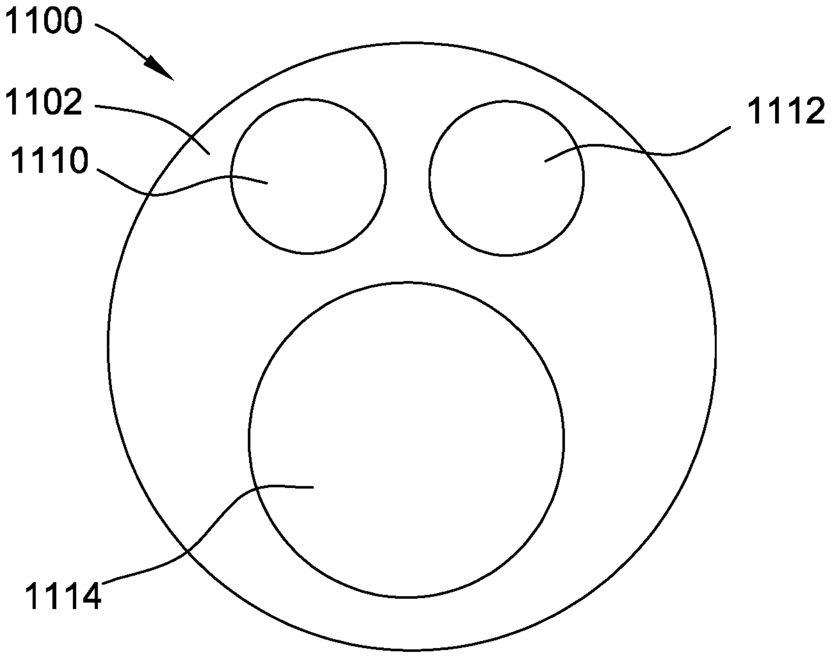
FIG. 11 is an end view of another embodiment of a multi-lumen arrangement.

FIG. 11 is an end view of another embodiment of a multi-lumen arrangement 1100. In the embodiment shown in FIG. 11, multi-lumen arrangement 1100 includes a tube 1102 (e.g., formed by variable diameter loop 150 and/or shaft 44) that defines three lumens: a first lumen 1110, a second lumen 1112, and a third lumen 1114. In this embodiment, cross-sections of lumens 1110, 1112, and 1114 are generally circular. Alternatively, lumens 1110, 1112, and 1114 may have any suitable shape.

In this embodiment, electrical wires having a first polarity (e.g., positive electrical wires) are routed through first lumen 1110, and electrical wires having a second polarity (e.g., negative electrical wires) are routed through second lumen 1112. Thus, electrical wires having different polarities are located in different lumens, electrically isolating them from one another. Further, in this embodiment, the shaping wire and activation wire are routed through third lumen 1114. Thus, the shaping and activation wires are separated from the electrical wires. Additional wires (e.g., a wire for magnetic sensor 302) may also be routed through third lumen 1114.

The multi-lumen embodiments described herein enable routing wires to help prevent electrical breakdown between electrical wires carrying high current and voltage. It also results in a more accurate and consist assembly process, reducing scraps and breaks in electrical wires. By routing different types of wires through different lumens, the chances of human error and device failure are reduced, and assembly time and costs are reduced as well.

Another technique for ensuring sufficient isolation is to use robust insulation on the electrical wires. Electrical wires in at least some known medical devices may have at most, for example, insulation having a thickness of approximately 0.0007 inches (0.01778 millimeters). However, in the systems and methods described herein, the insulation on electrical wires may have a thickness of, for example, up to approximately 0.0015 inches (0.0381 millimeters). This is roughly double the insulation of electrical wires in at least some known medical devices. The added thickness results in higher dielectric strength from the added material, and a substantially increased wire durability and strength to protect from abrasions, gouges, scratches, or other damage. This results in a consistent and reliable increase in the total dielectric strength of the electrical wires.

In other embodiments, physical separation of electrical wire pairs (to achieve added dielectric strength and isolation) may be achieved using various tubing arrangements. For example, a tubing made of a non-conductive or insulative material may be extended along the length of the wires throughout at least a portion of variable diameter loop 150 and/or shaft 44, providing physical separation and a barrier between electrical wire pairs as needed. The tubing may be, for example, fabricated from a heat shrink material such as polyethylene terephthalate (PET), polytetrafluoroethylene (PTFE), fluorinated ethylene propylene (FEP), or other suitable materials. Alternatively, the tubing may be fabricated from fully expanded or extruded tubing without any shrinking capabilities. The material used for tubing may be selected, for example, based on space and/or fitting concerns for the quantity of electrical wires to be routed or the size of the catheter itself.

Figure 12:
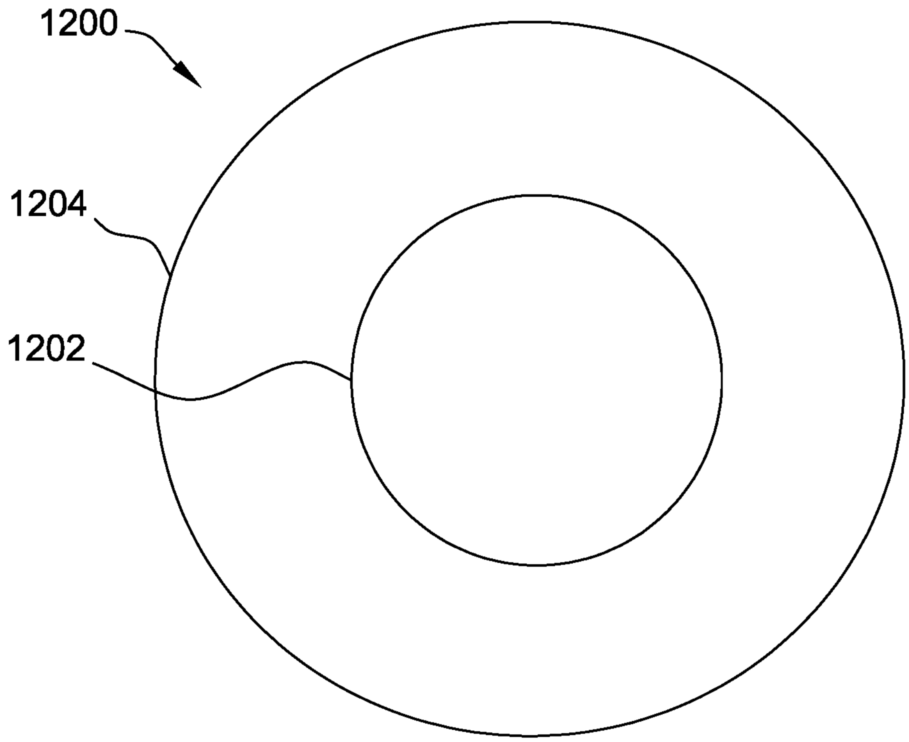
FIG. 12 is a schematic diagram of one embodiment of a tubing arrangement.

Pairs of tubing may be used to separate positive and negative wires. For example, FIG. 12 is a schematic diagram of one embodiment of a tubing arrangement 1200. In this embodiment, a first tube 1202 and a second tube 1204 are arranged coaxially. To provide physical isolation, first wires (e.g., positive electrical wires) may be routed within first tube 1202, and second wires (e.g., negative electrical wires) may be routed within second tube 1204 but outside of first tube 1202.

Figure 13:
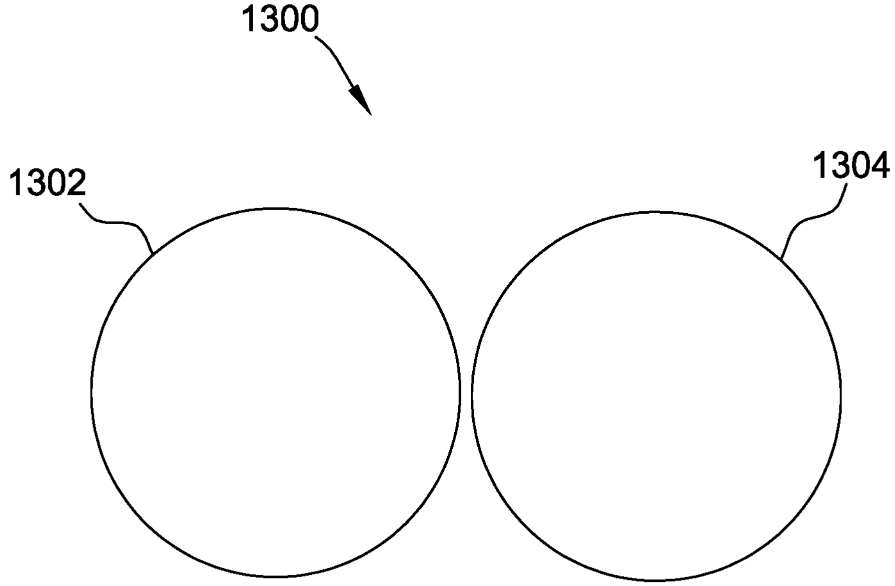
FIG. 13 is a schematic diagram of another embodiment of a tubing arrangement.

FIG. 13 is a schematic diagram of another embodiment of a tubing arrangement 1300. In this embodiment, a first tube 1302 and a second tube 1304 are arranged biaxially. To provide physical isolation, a first set of wires (e.g., positive electrical wires) may be routed within first tube 1302, and a second set of wires (e.g., negative electrical wires) may be routed within second tube 1304.

Figure 14:
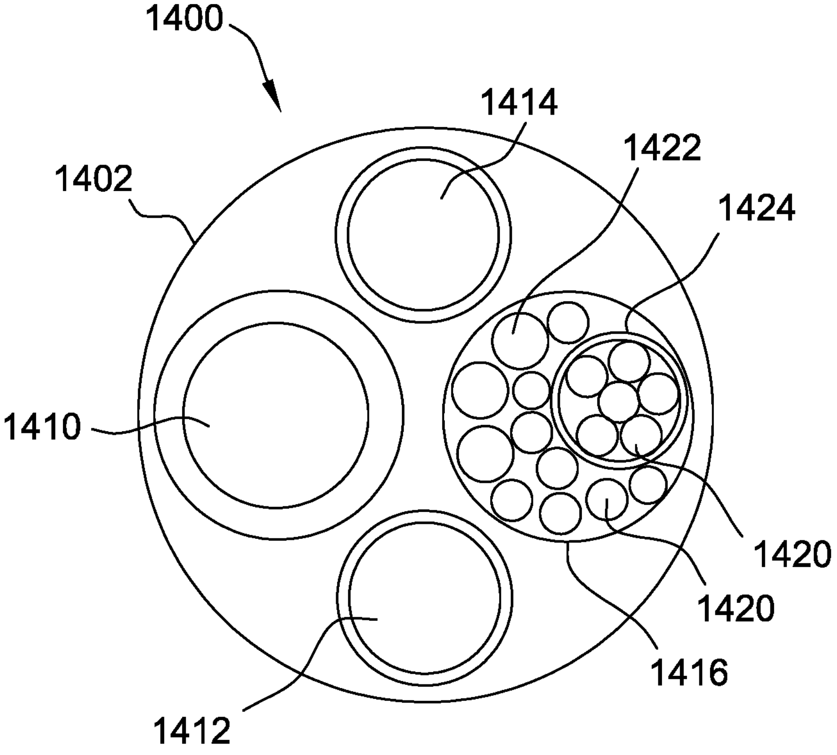
FIG. 14 is an end view of one embodiment of a catheter section.

FIG. 14 is an end view of one embodiment of a catheter section 1400 (e.g., within variable diameter loop 150 and/or shaft 44) including a tube 1402 defining a first lumen 1410, a second lumen 1412, a third lumen 1414, and a fourth lumen 1416. As shown in FIG. 14, a plurality of electrical wires 1420 and sensor wires 1422 are routed through fourth lumen 1416. In this embodiment, a tubing 1424 also extends through fourth lumen 1416. Further, a first set of electrical wires 1420 (e.g., positive electrical wires) are located within tubing 1420, and a second set of electrical wires 1420 (e.g., negative electrical wires) ore located outside tubing 1424. Tubing 1424 may be fabricated from, for example, a heat shrink material, as described above.

Figure 15:
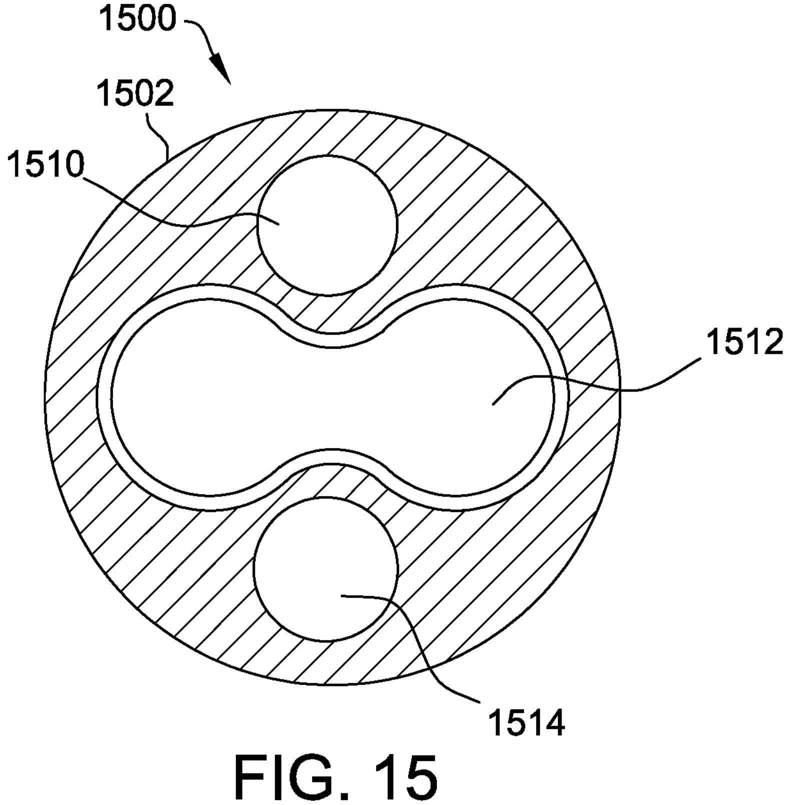
FIG. 15 is an end view of another embodiment of a catheter section.

FIG. 15 is an end view of another embodiment of a catheter section 1500 (e.g., within variable diameter loop 150 and/or shaft 44). As compared to catheter section 1400, catheter section 1500 eliminates a wall between two lumens such that catheter section 1500 only includes a first lumen 1510, a second lumen 1512, and a third lumen 1514. Due to the missing wall, this may be referred to as a 'ghost lumen' configuration.

Figure 16:
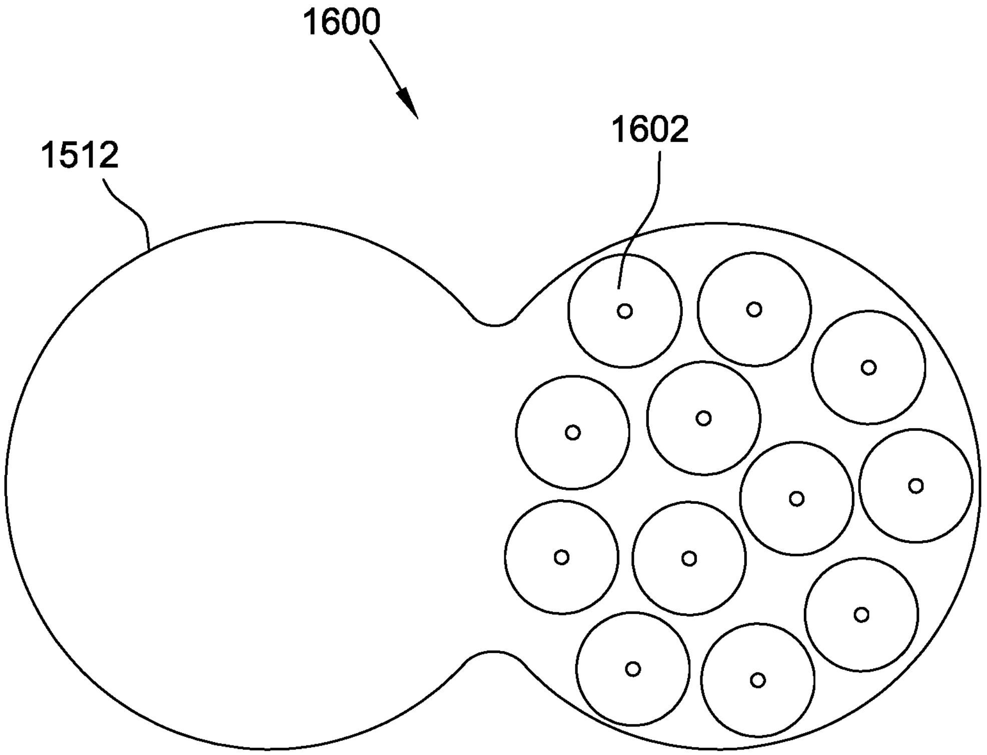
FIG. 16 is an end view of one embodiment of a wiring arrangement within the second lumen shown in FIG. 15.

FIG. 16 is an end view of one embodiment of a wiring arrangement 1600 within second lumen 1512. In this embodiment, electrical wires 1602 are not physically isolated from one another with tubing. Accordingly, electrical wires 1602 should each include sufficient insulation (e.g., such as that described above) to ensure sufficient isolation from electrical wire pairs.

Figure 17:
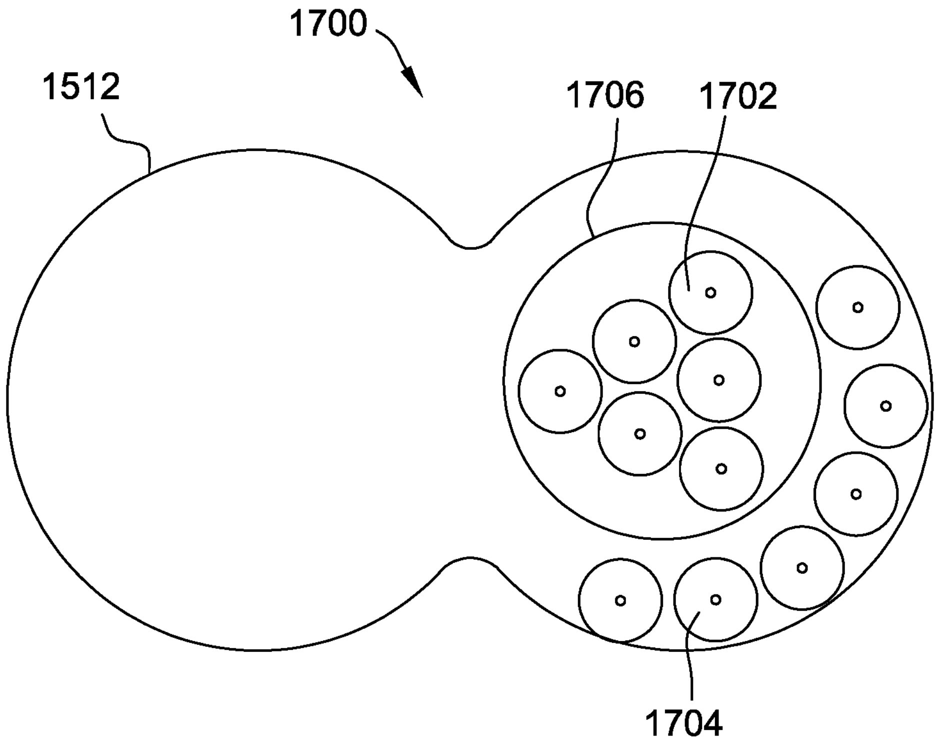
FIG. 17 is an end view of another embodiment of a wiring arrangement within the second lumen shown in FIG. 15.

FIG. 17 is an end view of another embodiment of a wiring arrangement 1700 within second lumen 1512. In this embodiment, a first set 1702 of electrical wires (e.g., positive wires) are separated from a second set 1704 of electrical wires (e.g., negative wires) by a tube 1706.

Figure 18:
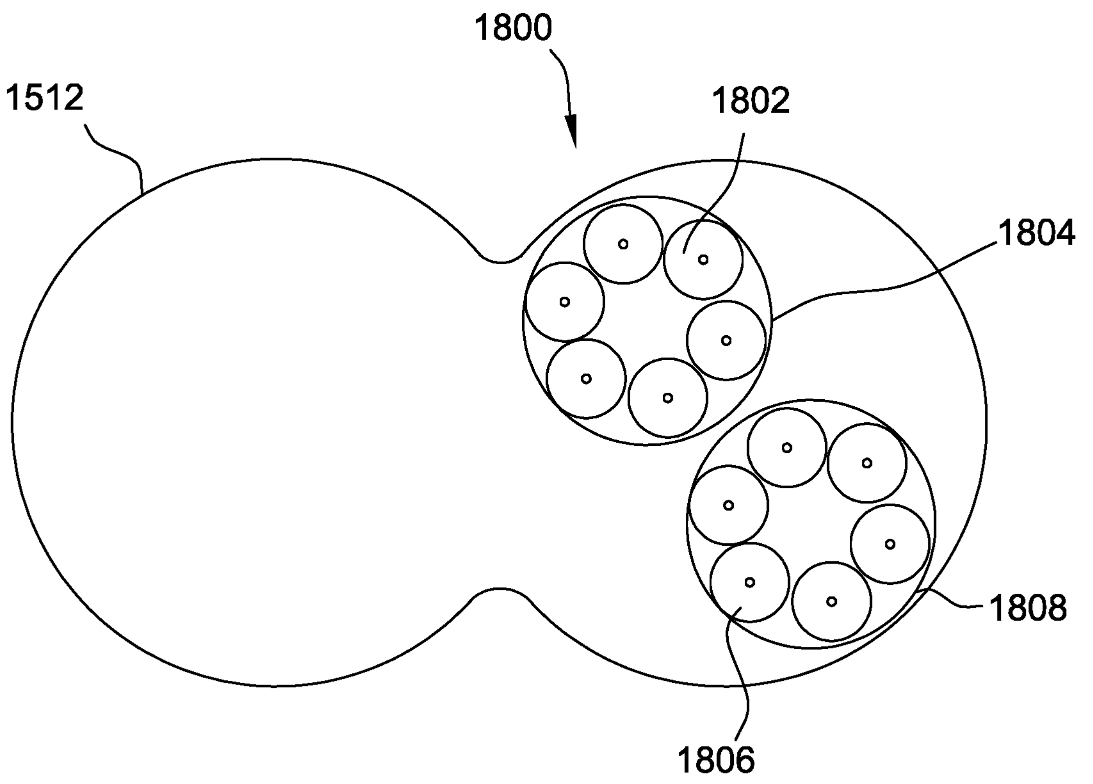
FIG. 18 is an end view of another embodiment of a wiring arrangement within the second lumen shown in FIG. 15.

FIG. 18 is an end view of another embodiment of a wiring arrangement 1800 within second lumen 1512. In this embodiment, a first set 1802 of electrical wires (e.g., positive wires) are enclosed in a first tube 1804, and a second set 1806 of electrical wires (e.g., negative wires) are enclosed in a second tube 1808.

In some embodiments, to prevent electrical wires from dielectric breakdown, the amount of conductive fluid that the interior of catheter (e.g., the interior of variable diameter loop 150 and/or shaft 44) is exposed to is reduced. The conductive fluid may be, for example, saline or blood. To reduce the expose to conductive fluid, a sealant or filler material may be applied inside of the variable diameter loop 150 and/or shaft 44. The material may be, for example, silicone gel, urethane gel, or other suitable compliant and/or viscous materials. In one embodiment, the filler material is injected into a catheter section from a distal end of the catheter section, and an indicator hole (not shown) located at a proximal end of the catheter section facilitates determining when a complete fill is achieved.

Another technique for reducing the exposure to conductive fluid (and to prevent electrical wires from dielectric breakdown) is to eliminate, patch, seal, and/or reflow exposed holes in variable diameter loop 150 and/or shaft 44. These holes may be originally included, for example, to facilitate routing the various wires through variable diameter loop 150 and/or shaft 44. However, once the wires have been routed, these holes can be closed to reduce exposure to conductive fluid. In one embodiment, a suitable epoxy (e.g., urethane epoxy) is applied to each hole pierce. In another embodiment, RF energy is applied to catheter electrodes 144 in variable diameter loop 150. The application of RF energy causes thermoplastic material proximate catheter electrodes 144 to flow into and around holes in the vicinity. Applying the RF electrode material also has an additional benefit of embedding catheter electrodes 144 and corresponding wires more thoroughly within catheter 14, and sealing the edges of catheter electrodes 144 as well.

Figure 19:
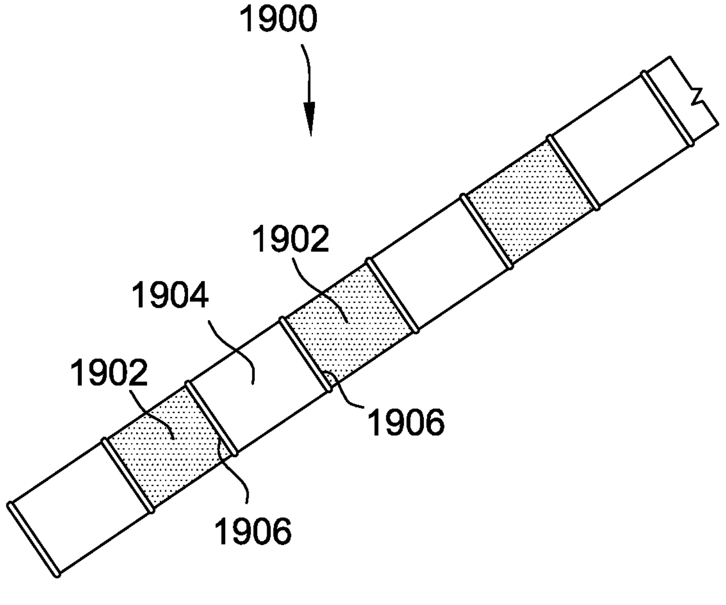
FIG. 19 is a perspective view of a catheter section.

For example, FIG. 19 is a perspective view of a catheter section 1900 including a plurality of electrodes 1902. In catheter section 1900, RF energy has been applied to electrodes 1902, causing thermoplastic material 1904 proximate electrodes to flow and generate sealing ridges 1906 at edges of electrodes 1902.

Figure 20A:
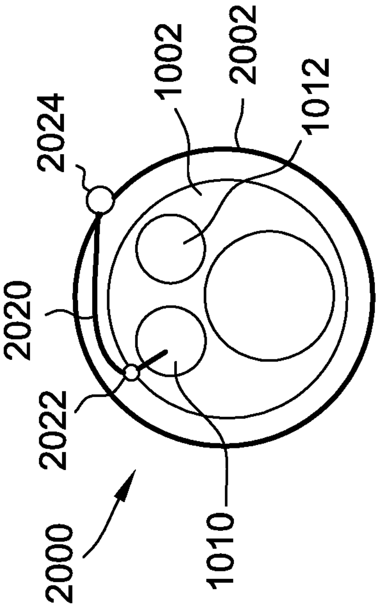
FIG. 20A is an end schematic view of a wiring arrangement that may be used with multi-lumen arrangement shown in FIG. 10.
Figure 20B:
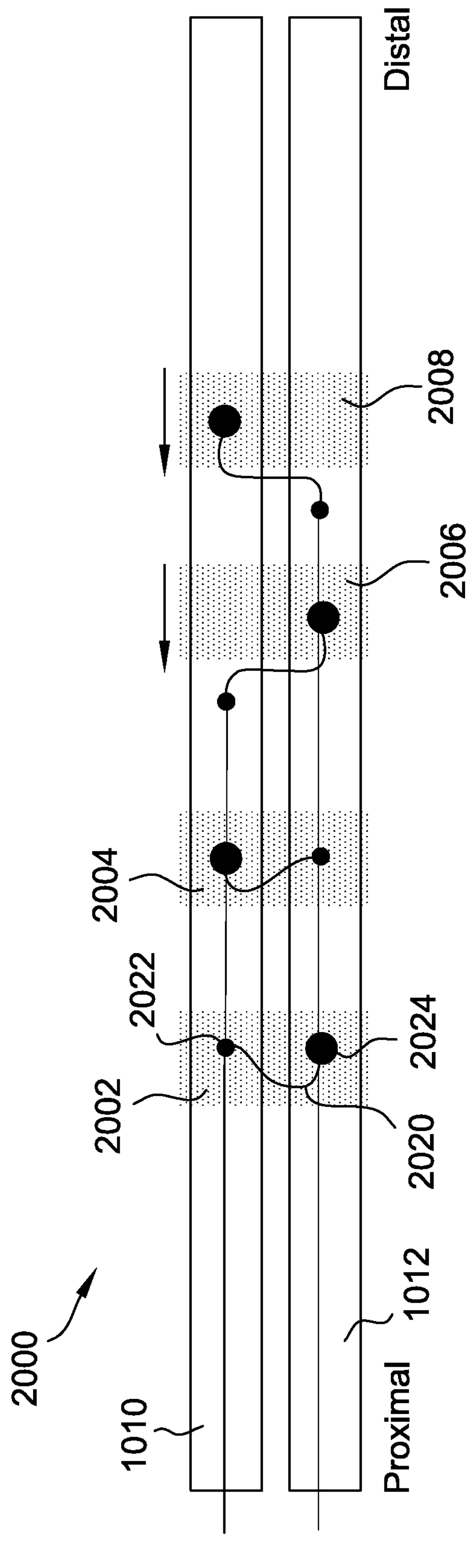
FIG. 20B is an axial schematic view of the wiring arrangement shown in FIG. 20A.

FIG. 20A is an end schematic view of a wiring arrangement 2000 that may be used with multi-lumen arrangement 1000 (shown in FIG. 10) within variable diameter loop 150. FIG. 20B is an axial schematic view of wiring arrangement 2000. Those of skill in the art will appreciate that wiring arrangement 2000 may similarly be used with the other multi-lumen arrangements described herein.

In this embodiment, wiring arrangement 2000 facilitates providing wiring for twelve ring electrodes. For clarity, only a twelfth electrode 2002, eleventh electrode 2004, tenth electrode 2006, and ninth electrode 2008 are shown. Further, in this embodiment, wires for even electrodes (e.g., including twelfth electrode 2002 and tenth electrode 2006) are routed through first lumen 1010, and wires for odd electrodes (e.g., including eleventh electrode 2004 and ninth electrode 2008) are routed through second lumen 1012.

In wiring arrangement 2000, the electrode wires for each electrode exit the associated lumen through a corresponding hole in tube 1002, and extend at least partially circumferentially around tube 1002 to a weld on the corresponding electrode.

For example, as shown in FIGS. 20A and 20B, a twelfth electrode wire 2020 (corresponding to twelfth electrode 2002) exits first lumen 1010 through a hole 2022 defined through tube 1002. Hole 2022 may be formed, for example, by piercing tube 1002. Once twelfth electrode wire 2020 exits tube 1002, twelfth electrode wire 2020 extends partially circumferentially around tube 1002, and terminates at a weld 2024 on twelfth electrode 2002.

In the embodiment shown in FIGS. 20A and 20B, the welds are located proximate the lumen that did not contain the corresponding electrode wire. That is, weld 2024 is located proximate second lumen 1012, while twelfth electrode wire 2020 is routed through first lumen 1010. Alternatively, the weld may be located at any suitable location, as long as the corresponding electrode wire extends at least partially circumferentially around tube 1002.

Further, in this embodiment, electrode wires coming out of first lumen 1010 extend partially circumferentially in a first direction (e.g., clockwise), while electrode wires coming out of second lumen 1012 extend partially circumferentially in a second, opposite direction (e.g., counterclockwise). Alternatively, the electrode wires may all extend in the same direction, or may each extend in any suitable direction.

In addition, it should be noted that in FIG. 20B, tenth electrode 2006 and ninth electrode 2008 are not shown in their final position, Rather, to complete manufacturing, tenth electrode 2006 and ninth electrode 2008 would be shifted axially in a proximal direction before being affixed to tube 1002, as indicated by the two arrows shown in FIG. 20B.

Extending electrode wires partially circumferentially around tube 1002 may provide benefits. For example, the ends of electrode wires typically each include an exposed conductor (e.g., bare copper). By extending the electrode wires as shown, any exposed conductor is located outside of first and second lumens 1010 and 1012. This prevents the exposed conductor from contacting fluids that may ingress into first and second lumens 1010 and 1012.

Those of skill in the art will appreciate that the various embodiments described herein for isolating wires from one another may be implemented independently from one another or in any suitable combination.

The embodiments described herein provide systems and methods for electroporation catheters. An electroporation catheter includes a shaft, and a variable diameter loop coupled to a distal end of the shaft, the variable diameter loop including a plurality of electrodes. The catheter further includes a plurality of electrical wires connected to the plurality of electrodes and extending through the variable diameter loop and the shaft, the plurality of electrical wires configured to energize the plurality of electrodes, and a multi-lumen arrangement extending through at least a portion of at least one of the shaft and the variable diameter loop. The multi-lumen arrangement includes a first lumen housing a first subset of the plurality of electrical wires, and a second lumen housing a second subset of the plurality of electrical wires.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electroporation catheter comprising:

a shaft comprising a proximal end and a distal end;

a plurality of electrodes coupled to the distal end of the shaft;

a plurality of electrical wires connected to the plurality of electrodes and extending through the shaft, the plurality of electrical wires configured to energize the plurality of electrodes; and a multi-lumen arrangement extending through at least a portion of the shaft, the multi-lumen arrangement comprising:

a first lumen housing a first subset of the plurality of electrical wires and a tube, the tube extending through a portion of the first lumen, the plurality of electrical wires comprising a first subset housed inside the tube and a second subset housed in the first lumen and outside the tube, wherein the second subset of the plurality of electrical wires conform to the shape of the first lumen; and a second lumen outside of the first lumen.

2. The electroporation catheter in accordance with claim 1, further comprising a shaping wire and an activation wire extending through the shaft, wherein the multi-lumen arrangement further comprises a third lumen housing the shaping wire and the activation wire.

3. The electroporation catheter in accordance with claim 1, wherein cross-sections of the first lumen are generally circular or peanut shaped.

4. The electroporation catheter in accordance with claim 3, wherein the peanut-shaped lumen comprises a first circular portion and a second circular portion, wherein the tube and the plurality of electrical wires extend through the first circular portion.

5. The electroporation catheter in accordance with claim 1, wherein the multi-lumen arrangement further comprises at least one dummy lumen that does not house any wires.

6. The electroporation catheter in accordance with claim 1, wherein at least one of the electrical wires includes insulation having a thickness of approximately 0.0015 inches (0.0381 millimeters).

7. The electroporation catheter in accordance with claim 1, further comprising a filler material injected within the shaft.

8. The electroporation catheter in accordance with claim 1, further comprising at least one seal formed at an edge of at least one of the plurality of electrodes, the at least one seal configured to prevent conductive fluids from entering an interior of the shaft.

9. The electroporation catheter in accordance with claim 1, wherein at least one of the electrical wires extends out of the multi-lumen arrangement, and at least partially circumferentially around the multi-lumen arrangement, before terminating at the associated electrode.

10. The electroporation catheter in accordance with claim 1, wherein the second subset of the plurality of electrical wires wrap at least partially around the tube housing the first subset of the plurality of electrical wires.

11. The electroporation catheter in accordance with claim 10, wherein the second subset of the plurality of electrical wires and the tube housing the first subset of the plurality of electrical wires together conform to the shape of the first lumen.

12. The electroporation catheter in accordance with claim 10, wherein the second subset of the plurality of electrical wires are unrestrained within the first lumen.

13. The electroporation catheter in accordance with claim 10, wherein the second subset of the plurality of electrical wires have a non-circular cross-section.

14. The electroporation catheter in accordance with claim 13, wherein the non-circular cross-section comprises a C-shape.

15. The electroporation catheter in accordance with claim 1, wherein the second subset of the plurality of electrical wires is not contained in a tube other than the first lumen.

16. The electroporation catheter in accordance with claim 1, wherein the second subset of the plurality of electrical wires is in direct contact with an inner wall of the first lumen.

17. The electroporation catheter in accordance with claim 1, wherein the tube and the second subset of the plurality of electrical wires together fill substantially all of the cross-sectional area of the first lumen.

18. An electroporation catheter comprising:

a shaft comprising a proximal end and a distal end;

a plurality of electrodes coupled to the distal end of the shaft;

a plurality of electrical wires connected to the plurality of electrodes and extending through the shaft, the plurality of electrical wires configured to energize the plurality of electrodes; and a tubing arrangement extending through a portion of a first lumen, the tubing arrangement comprising:

a first tube housing a first subset of the plurality of electrical wires, wherein a second subset of the plurality of electrical wires are outside of the first tube and located in the first lumen, wherein the second subset of the plurality of electrical wires conform to the shape of the first lumen, the second subset of the plurality of electrical wires are physically isolated from the first subset of the plurality of electrical wires.

19. The electroporation catheter in accordance with claim 18, wherein the first tube comprises a heat shrink material.

20. The electroporation catheter in accordance with claim 18, further comprising a second tube, wherein the first tube is positioned within the second tube.

21. The electroporation catheter in accordance with claim 18, further comprising a second tube, wherein the first tube and the second tube are arranged biaxially.

22. The electroporation catheter in accordance with claim 18, wherein at least one of the electrical wires includes insulation having a thickness of approximately 0.0015 inches (0.0381 millimeters).

23. The electroporation catheter in accordance with claim 18, further comprising a filler material injected within the shaft.

24. The electroporation catheter in accordance with claim 18, further comprising at least one seal formed at an edge of at least one of the plurality of electrodes, the at least one seal configured to prevent conductive fluids from entering an interior of the shaft.

25. A method of assembling an electroporation catheter, the method comprising;

coupling a shaft to a plurality of electrodes, the shaft comprising a first lumen and a second lumen;

connecting a plurality of electrical wires to the plurality of electrodes, the plurality of electrical wires extending through the shaft, the plurality of electrical wires configured to energize the plurality of electrodes; and passing the plurality of electrical wires through the first lumen, the plurality of electrical wires comprising a first subset and a second subset, wherein passing the plurality of electrical wires through the first lumen comprises:

passing the first subset of electrical wires through a first tube extending through a portion of the first lumen; and passing the second subset of electrical wires through the first lumen and outside of the first tube to physically isolate the first subset of the plurality of electrical wires from the second subset of the plurality of electrical wires, wherein the second subset of electrical wires conform to the shape of the first lumen.

26. The method in accordance with claim 25, further comprising injecting a filler material into the shaft.

27. The method in accordance with claim 25, further comprising forming a seal on the shaft to facilitate preventing exposure of the plurality of electrical wires to conductive fluid.

* * * * *